(12) United States Patent
Lambrecht et al.

(10) Patent No.: US 9,706,947 B2
(45) Date of Patent: Jul. 18, 2017

(54) METHOD OF PERFORMING AN ANCHOR IMPLANTATION PROCEDURE WITHIN A DISC

(75) Inventors: Gregory H. Lambrecht, Natick, MA (US); Robert Kevin Moore, Natick, MA (US); Jacob Einhorn, Brookline, MA (US)

(73) Assignee: Intrinsic Therapeutics, Inc., Woburn, MA (US)

( * ) Notice: Subject to any disclaimer, the term of this patent is extended or adjusted under 35 U.S.C. 154(b) by 0 days.

(21) Appl. No.: 13/017,812

(22) Filed: Jan. 31, 2011

(65) Prior Publication Data

US 2011/0125271 A1   May 26, 2011

Related U.S. Application Data

(63) Continuation of application No. 11/417,793, filed on May 3, 2006, now Pat. No. 7,879,097, which is a (Continued)

(51) Int. Cl.
*A61F 2/44* (2006.01)
*A61B 5/107* (2006.01)
(Continued)

(52) U.S. Cl.
CPC .... *A61B 5/1076* (2013.01); *A61B 17/320708* (2013.01); *A61B 17/70* (2013.01); *A61F 2/441* (2013.01); *A61F 2/442* (2013.01); *A61F 2/4611* (2013.01); *A61F 2/4657* (2013.01); *A61B 5/4514* (2013.01); *A61B 2017/00261* (2013.01); *A61B 2017/22077* (2013.01);
(Continued)

(58) Field of Classification Search
CPC ................ A61F 2/44–2/447; A61F 2/4611
USPC ............. 606/41, 86 A, 99; 623/17.11–17.16
See application file for complete search history.

(56) References Cited

U.S. PATENT DOCUMENTS

| 3,526,567 A | 9/1970 | Macone |
|---|---|---|
| 3,867,728 A | 2/1975 | Stubstad et al. |

(Continued)

FOREIGN PATENT DOCUMENTS

| EP | 0277678 | 8/1988 |
|---|---|---|
| EP | 0298233 | 1/1989 |

(Continued)

OTHER PUBLICATIONS

Ahlgren, B.D., et al., "Anular Incision Technique on the Strength and Multidirectional Flexibility of the Healing Intervertebral Disc," *Spine*, 19 (8) : 948-954 (1994).

(Continued)

*Primary Examiner* — Jan Christopher Merene
*Assistant Examiner* — Steven Cotroneo
(74) *Attorney, Agent, or Firm* — Knobbe Martens Olson & Bear LLP

(57) ABSTRACT

Methods of performing procedures within an intervertebral disc are disclosed. The methods include performing procedures such as implant delivery, tissue manipulation, tissue diagnostics, and therapeutic and diagnostic agent delivery at selected locations within intervertebral discs. In one embodiment, a method includes delivering an anchor and an implant within a functional spinal unit using a surgical device having at least one depth stop.

18 Claims, 15 Drawing Sheets

Related U.S. Application Data continuation of application No. 10/359,516, filed on Feb. 5, 2003, now Pat. No. 7,717,961, which is a continuation-in-part of application No. 10/020,507, filed on Dec. 11, 2001, now Pat. No. 6,821,276, said application No. 10/359,516 is a continuation-in-part of application No. 10/055,504, filed on Oct. 25, 2001, now Pat. No. 7,258,700, which is a continuation-in-part of application No. 10/325,320, filed on Dec. 19, 2002, now Pat. No. 7,124,761, which is a continuation of application No. 09/696,636, filed on Oct. 25, 2000, now Pat. No. 6,508,839, which is a continuation-in-part of application No. 09/642,450, filed on Aug. 18, 2000, now Pat. No. 6,482,235, which is a continuation-in-part of application No. 09/608,797, filed on Jun. 30, 2000, now Pat. No. 6,425,919.

(60) Provisional application No. 60/298,605, filed on Jun. 14, 2001, provisional application No. 60/311,586, filed on Aug. 10, 2001, provisional application No. 60/172,996, filed on Dec. 21, 1999, provisional application No. 60/161,085, filed on Oct. 25, 1999, provisional application No. 60/149,490, filed on Aug. 18, 1999.

(51) Int. Cl.
*A61B 17/3207* (2006.01)
*A61B 17/70* (2006.01)
*A61B 5/00* (2006.01)
*A61B 17/00* (2006.01)
*A61B 17/22* (2006.01)
*A61B 17/32* (2006.01)
*A61B 17/34* (2006.01)
*A61F 2/28* (2006.01)
*A61F 2/30* (2006.01)
*A61F 2/46* (2006.01)
*A61B 90/00* (2016.01)

(52) U.S. Cl.
CPC ............ *A61B 2017/320044* (2013.01); *A61B 2017/3445* (2013.01); *A61B 2090/061* (2016.02); *A61B 2090/062* (2016.02); *A61F 2/2846* (2013.01); *A61F 2/30723* (2013.01); *A61F 2/30907* (2013.01); *A61F 2/4601* (2013.01); *A61F 2002/2817* (2013.01); *A61F 2002/30062* (2013.01); *A61F 2002/30075* (2013.01); *A61F 2002/30131* (2013.01); *A61F 2002/30224* (2013.01); *A61F 2002/30228* (2013.01); *A61F 2002/30291* (2013.01); *A61F 2002/30462* (2013.01); *A61F 2002/30571* (2013.01); *A61F 2002/30583* (2013.01); *A61F 2002/30589* (2013.01); *A61F 2002/30677* (2013.01); *A61F 2002/30777* (2013.01); *A61F 2002/30785* (2013.01); *A61F 2002/444* (2013.01); *A61F 2002/448* (2013.01); *A61F 2002/4435* (2013.01); *A61F 2002/4627* (2013.01); *A61F 2002/4635* (2013.01); *A61F 2002/4658* (2013.01); *A61F 2002/4661* (2013.01); *A61F 2002/4662* (2013.01); *A61F 2210/0004* (2013.01); *A61F 2210/0061* (2013.01); *A61F 2210/0085* (2013.01); *A61F 2220/0075* (2013.01); *A61F 2230/0013* (2013.01); *A61F 2230/0069* (2013.01); *A61F 2230/0091* (2013.01); *A61F 2310/00017* (2013.01); *A61F 2310/00023* (2013.01); *A61F 2310/00029* (2013.01); *A61F 2310/0097* (2013.01); *A61F 2310/00293* (2013.01); *A61F 2310/00365* (2013.01); *A61F 2310/00976* (2013.01)

(56) References Cited

U.S. PATENT DOCUMENTS

| | | | |
|---|---|---|---|
| 3,875,595 A * | 4/1975 | Froning | A61F 2/442 623/17.12 |
| 3,921,632 A | 11/1975 | Bardani | |
| 3,997,138 A | 12/1976 | Crock et al. | |
| 4,041,550 A | 8/1977 | Frazier | |
| 4,078,559 A | 3/1978 | Nissinen | |
| 4,280,954 A | 7/1981 | Yannas et al. | |
| 4,349,921 A | 9/1982 | Kuntz | |
| 4,365,357 A | 12/1982 | Draenert | |
| 4,473,070 A | 9/1984 | Matthews et al. | |
| 4,502,161 A | 3/1985 | Wall | |
| 4,532,926 A | 8/1985 | O'Holla | |
| 4,573,454 A | 3/1986 | Hoffman | |
| 4,665,906 A | 5/1987 | Jervis | |
| 4,738,251 A | 4/1988 | Plaza | |
| 4,741,330 A | 5/1988 | Hayhurst | |
| 4,743,256 A | 5/1988 | Brantigan | |
| 4,744,364 A | 5/1988 | Kensey | |
| 4,755,184 A | 7/1988 | Silverberg | |
| 4,772,287 A | 9/1988 | Ray et al. | |
| 4,781,190 A | 11/1988 | Lee | |
| 4,798,205 A | 1/1989 | Bonomo et al. | |
| 4,815,453 A | 3/1989 | Cotrel | |
| 4,821,942 A | 4/1989 | Richards et al. | |
| 4,837,285 A | 6/1989 | Berg et al. | |
| 4,852,568 A | 8/1989 | Kensey | |
| 4,854,304 A | 8/1989 | Zielke | |
| 4,863,477 A | 9/1989 | Monson | |
| 4,871,094 A | 10/1989 | Gall et al. | |
| 4,873,976 A | 10/1989 | Schreiber | |
| 4,874,389 A | 10/1989 | Downey | |
| 4,890,612 A | 1/1990 | Kensey | |
| 4,904,260 A | 2/1990 | Ray et al. | |
| 4,911,718 A | 3/1990 | Lee et al. | |
| 4,917,704 A | 4/1990 | Frey et al. | |
| 4,919,667 A | 4/1990 | Richmond | |
| 4,932,969 A | 6/1990 | Frey et al. | |
| 4,936,844 A | 6/1990 | Chandler et al. | |
| 4,946,378 A | 8/1990 | Hirayama et al. | |
| 4,946,467 A | 8/1990 | Ohi et al. | |
| 4,955,908 A | 9/1990 | Frey et al. | |
| 4,994,073 A | 2/1991 | Green et al. | |
| 5,002,576 A | 3/1991 | Fuhrmann et al. | |
| 5,007,909 A | 4/1991 | Rogozinski | |
| 5,015,255 A | 5/1991 | Kuslich | |
| 5,021,059 A | 6/1991 | Kensey et al. | |
| 5,035,716 A | 7/1991 | Downey | |
| 5,046,513 A | 9/1991 | Gatturna et al. | |
| 5,047,055 A | 9/1991 | Bao et al. | |
| 5,053,046 A | 10/1991 | Janese | |
| 5,059,206 A | 10/1991 | Winters | |
| 5,061,274 A | 10/1991 | Kensey | |
| 5,071,437 A | 12/1991 | Steffee | |
| 5,100,422 A | 3/1992 | Berguer et al. | |
| 5,108,420 A | 4/1992 | Marks | |
| 5,108,438 A | 4/1992 | Stone | |
| 5,116,357 A | 5/1992 | Eberbach | |
| 5,122,155 A | 6/1992 | Eberbach | |
| 5,123,926 A | 6/1992 | Pisharodi | |
| 5,129,906 A | 7/1992 | Ross et al. | |
| 5,141,515 A | 8/1992 | Eberbach | |
| 5,147,374 A | 9/1992 | Fernandez | |
| 5,147,387 A | 9/1992 | Jansen et al. | |
| 5,171,252 A | 12/1992 | Friedland | |
| 5,171,259 A | 12/1992 | Inoue | |
| 5,171,279 A | 12/1992 | Mathews | |
| 5,171,280 A | 12/1992 | Baumgartner | |
| 5,171,281 A | 12/1992 | Parsons et al. | |
| 5,176,692 A | 1/1993 | Wilk et al. | |
| 5,180,393 A | 1/1993 | Commarmond | |

(56) References Cited

U.S. PATENT DOCUMENTS

| | | |
|---|---|---|
| 5,189,789 A | 3/1993 | Hall |
| 5,192,300 A | 3/1993 | Fowler |
| 5,192,301 A | 3/1993 | Kamiya et al. |
| 5,192,326 A | 3/1993 | Bao et al. |
| 5,201,729 A | 4/1993 | Hertzmann et al. |
| 5,203,787 A | 4/1993 | Noblitt et al. |
| 5,207,649 A | 5/1993 | Aruny |
| 5,217,471 A | 6/1993 | Burkhart |
| 5,219,359 A | 6/1993 | McQuilkin et al. |
| 5,222,962 A | 6/1993 | Burkhart |
| 5,222,974 A | 6/1993 | Kensey et al. |
| 5,236,438 A | 8/1993 | Wilk |
| 5,239,982 A | 8/1993 | Trauthen |
| 5,242,448 A | 9/1993 | Pettine et al. |
| 5,254,133 A | 10/1993 | Seid |
| 5,258,000 A | 11/1993 | Gianturco |
| 5,258,031 A | 11/1993 | Salib et al. |
| 5,258,043 A | 11/1993 | Stone |
| 5,269,783 A | 12/1993 | Sander |
| 5,282,827 A | 2/1994 | Kensey et al. |
| 5,292,332 A | 3/1994 | Lee |
| 5,306,311 A | 4/1994 | Stone et al. |
| 5,312,435 A | 5/1994 | Nash et al. |
| 5,320,633 A | 6/1994 | Allen et al. |
| 5,320,644 A | 6/1994 | Baumgartner |
| 5,342,393 A | 8/1994 | Stack |
| 5,342,394 A | 8/1994 | Matsuno et al. |
| 5,352,224 A | 10/1994 | Westermann |
| 5,356,432 A | 10/1994 | Rutkow et al. |
| 5,366,460 A | 11/1994 | Eberbach |
| 5,368,602 A | 11/1994 | de la Torre |
| 5,370,697 A | 12/1994 | Baumgartner |
| 5,383,477 A | 1/1995 | DeMatteis |
| 5,383,905 A | 1/1995 | Golds et al. |
| 5,387,213 A | 2/1995 | Breard et al. |
| 5,391,182 A | 2/1995 | Chin |
| 5,397,331 A | 3/1995 | Himpens et al. |
| 5,397,332 A | 3/1995 | Kammerer et al. |
| 5,397,355 A | 3/1995 | Marin et al. |
| 5,405,360 A | 4/1995 | Tovey |
| 5,425,773 A | 6/1995 | Boyd et al. |
| 5,431,658 A | 7/1995 | Moskovich |
| 5,437,631 A | 8/1995 | Janzen |
| 5,445,639 A | 8/1995 | Kuslich et al. |
| 5,456,720 A | 10/1995 | Schultz et al. |
| 5,464,407 A | 11/1995 | McGuire |
| 5,478,353 A | 12/1995 | Yoon |
| 5,500,000 A | 3/1996 | Feagin et al. |
| 5,507,754 A | 4/1996 | Green et al. |
| 5,514,130 A | 5/1996 | Baker |
| 5,514,180 A | 5/1996 | Heggeness et al. |
| 5,520,700 A | 5/1996 | Beyar et al. |
| 5,522,898 A | 6/1996 | Bao et al. |
| 5,531,759 A | 7/1996 | Kensey et al. |
| 5,534,028 A | 7/1996 | Bao et al. |
| 5,534,030 A | 7/1996 | Navarro et al. |
| 5,545,178 A | 8/1996 | Kensey et al. |
| 5,545,229 A | 8/1996 | Parsons et al. |
| 5,549,617 A | 8/1996 | Green et al. |
| 5,549,679 A * | 8/1996 | Kuslich ............ 623/17.12 |
| 5,552,100 A | 9/1996 | Shannon et al. |
| 5,556,428 A | 9/1996 | Shah |
| 5,556,429 A | 9/1996 | Felt |
| 5,562,689 A | 10/1996 | Green et al. |
| 5,562,735 A | 10/1996 | Margulies |
| 5,562,736 A | 10/1996 | Ray et al. |
| 5,562,738 A | 10/1996 | Boyd et al. |
| 5,569,252 A | 10/1996 | Justin et al. |
| 5,571,139 A | 11/1996 | Jenkins, Jr. |
| 5,571,189 A | 11/1996 | Kuslich |
| 5,582,616 A | 12/1996 | Bolduc et al. |
| 5,591,204 A | 1/1997 | Janzen et al. |
| 5,591,223 A | 1/1997 | Lock et al. |
| 5,591,235 A | 1/1997 | Kuslich |
| 5,609,634 A | 3/1997 | Voydeville |
| 5,611,801 A | 3/1997 | Songer |
| 5,613,974 A | 3/1997 | Andreas et al. |
| 5,620,012 A | 4/1997 | Benderev et al. |
| 5,624,463 A | 4/1997 | Stone et al. |
| 5,626,613 A | 5/1997 | Schmieding |
| 5,634,931 A | 6/1997 | Kugel |
| 5,634,936 A | 6/1997 | Linden et al. |
| 5,641,373 A | 6/1997 | Shannon et al. |
| 5,645,084 A | 7/1997 | McKay |
| 5,645,597 A | 7/1997 | Krapiva |
| 5,649,926 A | 7/1997 | Howland |
| 5,658,286 A | 8/1997 | Sava |
| 5,658,343 A | 8/1997 | Hauselmann et al. |
| 5,662,683 A | 9/1997 | Kay |
| 5,669,935 A | 9/1997 | Rosenman et al. |
| 5,674,294 A | 10/1997 | Bainville et al. |
| 5,674,295 A | 10/1997 | Ray et al. |
| 5,674,296 A | 10/1997 | Bryan et al. |
| 5,676,698 A | 10/1997 | Janzen et al. |
| 5,676,701 A | 10/1997 | Yuan et al. |
| 5,681,310 A | 10/1997 | Yuan et al. |
| 5,681,351 A | 10/1997 | Jamiolkowski et al. |
| 5,683,465 A | 11/1997 | Shinn et al. |
| 5,690,674 A | 11/1997 | Diaz |
| 5,695,525 A | 12/1997 | Mulhauser et al. |
| 5,702,450 A | 12/1997 | Bisserie |
| 5,702,451 A | 12/1997 | Biedermann et al. |
| 5,702,454 A | 12/1997 | Baumgartner |
| 5,702,462 A | 12/1997 | Oberlander |
| 5,704,936 A | 1/1998 | Mazel |
| 5,705,780 A | 1/1998 | Bao |
| 5,716,408 A | 2/1998 | Eldridge et al. |
| 5,716,409 A | 2/1998 | Debbas |
| 5,716,413 A | 2/1998 | Walter et al. |
| 5,716,416 A | 2/1998 | Lin |
| 5,725,577 A | 3/1998 | Saxon |
| 5,725,582 A | 3/1998 | Bevan et al. |
| 5,728,097 A | 3/1998 | Mathews |
| 5,728,150 A | 3/1998 | McDonald et al. |
| 5,730,744 A | 3/1998 | Justin et al. |
| 5,733,337 A | 3/1998 | Carr, Jr. et al. |
| 5,740,520 A | 4/1998 | Cyze et al. |
| 5,743,917 A | 4/1998 | Saxon |
| 5,746,755 A | 5/1998 | Wood et al. |
| 5,746,765 A | 5/1998 | Kleshinski et al. |
| 5,755,797 A | 5/1998 | Baumgartner |
| 5,766,246 A | 6/1998 | Mulhauser et al. |
| 5,769,864 A | 6/1998 | Kugel |
| 5,769,893 A | 6/1998 | Shah |
| 5,772,661 A | 6/1998 | Michelson |
| 5,776,183 A | 7/1998 | Kanesaka et al. |
| 5,782,831 A | 7/1998 | Sherman et al. |
| 5,782,844 A | 7/1998 | Yoon et al. |
| 5,785,705 A | 7/1998 | Baker |
| 5,800,549 A | 9/1998 | Bao et al. |
| 5,800,550 A | 9/1998 | Sertich |
| 5,810,851 A | 9/1998 | Yoon |
| 5,823,994 A | 10/1998 | Sharkey et al. |
| 5,824,008 A | 10/1998 | Bolduc et al. |
| 5,824,082 A | 10/1998 | Brown |
| 5,824,093 A * | 10/1998 | Ray et al. ............ 623/17.16 |
| 5,824,094 A | 10/1998 | Serhan et al. |
| 5,827,298 A | 10/1998 | Hart et al. |
| 5,836,315 A | 11/1998 | Benderev et al. |
| 5,843,082 A | 12/1998 | Yuan et al. |
| 5,843,084 A | 12/1998 | Hart et al. |
| 5,843,173 A | 12/1998 | Shannon et al. |
| 5,846,261 A | 12/1998 | Kotula et al. |
| 5,860,425 A | 1/1999 | Benderev et al. |
| 5,860,977 A | 1/1999 | Zucherman et al. |
| 5,865,845 A | 2/1999 | Thalgott |
| 5,865,846 A | 2/1999 | Bryan et al. |
| 5,888,220 A | 3/1999 | Felt et al. |
| 5,888,226 A | 3/1999 | Rogozinski |
| 5,893,889 A | 4/1999 | Harrington |
| 5,895,426 A | 4/1999 | Scarborough et al. |
| 5,911,701 A | 6/1999 | Miller et al. |
| 5,916,225 A | 6/1999 | Kugel |
| 5,919,235 A | 7/1999 | Husson et al. |

(56) References Cited

U.S. PATENT DOCUMENTS

| | | |
|---|---|---|
| 5,922,026 A | 7/1999 | Chin |
| 5,922,028 A | 7/1999 | Plouhar et al. |
| 5,928,279 A | 7/1999 | Shannon et al. |
| 5,928,284 A | 7/1999 | Mehdizadeh |
| 5,935,147 A | 8/1999 | Kensey et al. |
| 5,947,968 A | 9/1999 | Rogozinski |
| 5,954,716 A | 9/1999 | Sharkey et al. |
| 5,954,767 A | 9/1999 | Pajotin et al. |
| 5,957,939 A | 9/1999 | Heaven et al. |
| 5,961,545 A | 10/1999 | Lentz et al. |
| 5,972,000 A | 10/1999 | Beyar et al. |
| 5,972,007 A | 10/1999 | Sheffield et al. |
| 5,972,022 A | 10/1999 | Huxel |
| 5,976,174 A | 11/1999 | Ruiz |
| 5,976,186 A | 11/1999 | Bao et al. |
| 5,976,192 A | 11/1999 | McIntyre et al. |
| 5,980,504 A | 11/1999 | Sharkey et al. |
| 5,989,256 A | 11/1999 | Kuslich et al. |
| 5,993,448 A | 11/1999 | Remmler |
| 6,001,056 A | 12/1999 | Jassawalla et al. |
| 6,001,130 A | 12/1999 | Bryan et al. |
| 6,007,570 A | 12/1999 | Sharkey et al. |
| 6,007,575 A | 12/1999 | Samuels |
| 6,017,346 A | 1/2000 | Grotz |
| 6,019,792 A | 2/2000 | Cauthen |
| 6,019,793 A | 2/2000 | Perren et al. |
| 6,024,096 A | 2/2000 | Buckberg |
| 6,027,527 A | 2/2000 | Asano et al. |
| 6,066,175 A | 5/2000 | Henderson et al. |
| 6,073,051 A | 6/2000 | Sharkey et al. |
| 6,093,205 A * | 7/2000 | McLeod et al. ........... 623/17.16 |
| 6,093,207 A | 7/2000 | Pisharodi |
| 6,096,044 A | 8/2000 | Boyd et al. |
| 6,099,791 A | 8/2000 | Shannon et al. |
| 6,102,930 A | 8/2000 | Simmons, Jr. |
| 6,105,581 A | 8/2000 | Eggers et al. |
| 6,110,210 A | 8/2000 | Norton et al. |
| 6,113,639 A | 9/2000 | Ray et al. |
| 6,120,503 A | 9/2000 | Michelson |
| 6,120,539 A | 9/2000 | Eldridge et al. |
| 6,124,523 A | 9/2000 | Banas et al. |
| 6,126,682 A | 10/2000 | Sharkey et al. |
| 6,132,465 A | 10/2000 | Ray et al. |
| 6,140,452 A | 10/2000 | Felt et al. |
| 6,146,380 A | 11/2000 | Racz et al. |
| 6,146,420 A | 11/2000 | McKay |
| 6,153,292 A | 11/2000 | Bell et al. |
| 6,156,067 A | 12/2000 | Bryan et al. |
| 6,174,311 B1 | 1/2001 | Branch et al. |
| 6,174,323 B1 | 1/2001 | Biggs et al. |
| 6,179,836 B1 | 1/2001 | Eggers et al. |
| 6,180,848 B1 | 1/2001 | Flament et al. |
| 6,183,518 B1 | 2/2001 | Ross et al. |
| 6,187,048 B1 | 2/2001 | Milner et al. |
| 6,190,353 B1 | 2/2001 | Makower et al. |
| 6,190,414 B1 | 2/2001 | Young et al. |
| 6,203,735 B1 | 3/2001 | Edwin et al. |
| 6,206,921 B1 | 3/2001 | Guagliano et al. |
| 6,214,039 B1 | 4/2001 | Banas et al. |
| 6,224,630 B1 * | 5/2001 | Bao et al. .................. 623/17.16 |
| 6,224,631 B1 | 5/2001 | Kohrs et al. |
| 6,231,597 B1 | 5/2001 | Deem et al. |
| 6,235,059 B1 | 5/2001 | Benezech et al. |
| 6,240,926 B1 | 6/2001 | Chin Gan et al. |
| 6,241,722 B1 | 6/2001 | Dobak et al. |
| 6,245,099 B1 | 6/2001 | Edwin et al. |
| 6,245,107 B1 * | 6/2001 | Ferree ........................... 606/279 |
| 6,248,106 B1 | 6/2001 | Ferree |
| 6,258,086 B1 | 7/2001 | Ashley et al. |
| 6,264,659 B1 | 7/2001 | Ross et al. |
| 6,264,695 B1 | 7/2001 | Stoy |
| 6,267,834 B1 | 7/2001 | Shannon et al. |
| 6,273,912 B1 | 8/2001 | Scholz et al. |
| 6,280,475 B1 | 8/2001 | Bao et al. |
| 6,299,613 B1 | 10/2001 | Ogilvie et al. |
| 6,312,462 B1 | 11/2001 | McDermott et al. |
| RE37,479 E | 12/2001 | Kuslich |
| 6,325,805 B1 | 12/2001 | Ogilvie et al. |
| 6,340,369 B1 | 1/2002 | Ferree |
| 6,344,058 B1 | 2/2002 | Ferree et al. |
| 6,352,557 B1 | 3/2002 | Ferree |
| 6,355,063 B1 | 3/2002 | Calcote |
| 6,364,908 B1 | 4/2002 | Ysebaert |
| 6,371,990 B1 | 4/2002 | Ferree |
| 6,383,214 B1 | 5/2002 | Banas et al. |
| 6,387,130 B1 | 5/2002 | Stone et al. |
| 6,395,033 B1 | 5/2002 | Pepper |
| 6,398,803 B1 | 6/2002 | Layne et al. |
| 6,402,680 B2 | 6/2002 | Mortier et al. |
| 6,402,750 B1 | 6/2002 | Atkinson et al. |
| 6,406,420 B1 | 6/2002 | McCarthy et al. |
| 6,416,537 B1 | 7/2002 | Martakos et al. |
| 6,419,702 B1 | 7/2002 | Ferree |
| 6,419,704 B1 | 7/2002 | Ferree |
| 6,425,900 B1 | 7/2002 | Knodel et al. |
| 6,425,919 B1 | 7/2002 | Lambrecht et al. |
| 6,425,924 B1 | 7/2002 | Rousseau |
| 6,428,575 B2 | 8/2002 | Koo et al. |
| 6,428,576 B1 | 8/2002 | Haldimann |
| 6,436,143 B1 | 8/2002 | Ross et al. |
| 6,443,988 B2 | 9/2002 | Felt et al. |
| 6,454,804 B1 | 9/2002 | Ferree |
| 6,458,131 B1 | 10/2002 | Ray |
| 6,482,235 B1 | 11/2002 | Lambrecht et al. |
| 6,491,690 B1 | 12/2002 | Goble et al. |
| 6,503,269 B2 | 1/2003 | Nield et al. |
| 6,508,828 B1 | 1/2003 | Akerfeldt et al. |
| 6,508,839 B1 | 1/2003 | Lambrecht et al. |
| 6,514,194 B2 | 2/2003 | Schweich et al. |
| 6,520,967 B1 | 2/2003 | Cauthen |
| 6,530,932 B1 | 3/2003 | Swayze et al. |
| 6,530,933 B1 | 3/2003 | Yeung et al. |
| 6,537,198 B1 | 3/2003 | Vidlund et al. |
| 6,551,320 B2 | 4/2003 | Lieberman |
| 6,551,356 B2 | 4/2003 | Roussean |
| 6,558,387 B2 | 5/2003 | Errico et al. |
| 6,576,017 B2 | 6/2003 | Foley et al. |
| 6,579,291 B1 | 6/2003 | Keith et al. |
| 6,582,433 B2 | 6/2003 | Yun |
| 6,589,160 B2 | 7/2003 | Schweich et al. |
| 6,592,625 B2 * | 7/2003 | Cauthen .................... 623/17.16 |
| 6,599,311 B1 | 7/2003 | Biggs et al. |
| 6,607,530 B1 | 8/2003 | Carl et al. |
| 6,610,094 B2 | 8/2003 | Husson |
| 6,613,074 B1 | 9/2003 | Mitelberg et al. |
| 6,616,669 B2 | 9/2003 | Ogilvie et al. |
| 6,616,684 B1 | 9/2003 | Vidlund et al. |
| 6,620,196 B1 | 9/2003 | Trieu |
| 6,626,909 B2 | 9/2003 | Chin |
| 6,626,916 B1 | 9/2003 | Yeung et al. |
| 6,645,211 B2 | 11/2003 | Magana |
| 6,645,247 B2 | 11/2003 | Ferree |
| 6,648,903 B1 | 11/2003 | Pierson |
| 6,648,915 B2 | 11/2003 | Sazy |
| 6,648,918 B2 | 11/2003 | Ferree |
| 6,648,919 B2 | 11/2003 | Ferree |
| 6,648,920 B2 | 11/2003 | Ferree |
| 6,652,585 B2 | 11/2003 | Lange |
| 6,685,695 B2 | 2/2004 | Ferree |
| 6,689,125 B1 | 2/2004 | Keith et al. |
| 6,689,140 B2 | 2/2004 | Cohen |
| 6,712,853 B2 | 3/2004 | Kuslich |
| 6,719,797 B1 | 4/2004 | Ferree |
| 6,723,038 B1 | 4/2004 | Schroeder et al. |
| 6,726,696 B1 | 4/2004 | Houser et al. |
| 6,730,127 B2 | 5/2004 | Michelson |
| 6,733,496 B2 | 5/2004 | Sharkey et al. |
| 6,733,531 B1 | 5/2004 | Trieu |
| 6,733,534 B2 | 5/2004 | Sherman |
| 6,736,815 B2 | 5/2004 | Ginn |
| 6,749,605 B2 | 6/2004 | Ashley et al. |
| 6,755,777 B2 | 6/2004 | Schweich et al. |
| 6,783,546 B2 | 8/2004 | Zucherman et al. |
| 6,793,618 B2 | 9/2004 | Schweich et al. |

(56) References Cited

U.S. PATENT DOCUMENTS

| | | |
|---|---|---|
| 6,793,677 B2 | 9/2004 | Ferree |
| 6,805,695 B2 | 10/2004 | Keith et al. |
| 6,821,276 B2 | 11/2004 | Lambrecht et al. |
| 6,821,277 B2 | 11/2004 | Teitelbaum |
| 6,855,166 B2 | 2/2005 | Kohrs |
| 6,878,167 B2 | 4/2005 | Ferree |
| 6,883,520 B2 | 4/2005 | Lambrecht et al. |
| 6,893,466 B2 | 5/2005 | Trieu |
| 6,932,841 B2 | 8/2005 | Skylar et al. |
| 6,936,072 B2 | 8/2005 | Lambrecht et al. |
| 6,964,674 B1 | 11/2005 | Matsuura et al. |
| 6,966,910 B2 | 11/2005 | Ritland |
| 6,966,916 B2 | 11/2005 | Kumar |
| 6,969,404 B2 | 11/2005 | Ferree |
| 6,974,479 B2 | 12/2005 | Trieu |
| 6,984,247 B2 | 1/2006 | Cauthen |
| 6,986,771 B2 | 1/2006 | Paul et al. |
| 6,989,031 B2 | 1/2006 | Michelson |
| 6,997,953 B2 | 2/2006 | Chung et al. |
| 6,997,956 B2 | 2/2006 | Cauthen |
| 7,004,970 B2 | 2/2006 | Cauthen |
| 7,008,423 B2 | 3/2006 | Assaker et al. |
| 7,018,379 B2 | 3/2006 | Drewry et al. |
| 7,018,414 B2 | 3/2006 | Brau et al. |
| 7,025,771 B2 | 4/2006 | Kuslich et al. |
| 7,033,393 B2 | 4/2006 | Gainor et al. |
| 7,033,395 B2 | 4/2006 | Cauthen |
| 7,041,138 B2 | 5/2006 | Lange |
| 7,052,497 B2 | 5/2006 | Sherman et al. |
| 7,052,516 B2 | 5/2006 | Cauthen, III et al. |
| 7,056,345 B2 | 6/2006 | Kuslich |
| 7,077,862 B2 | 7/2006 | Vidlund et al. |
| 7,094,258 B2 | 8/2006 | Lambrecht et al. |
| 7,115,129 B2 | 10/2006 | Heggeness et al. |
| 7,124,761 B2 | 10/2006 | Lambrecht et al. |
| 7,144,397 B2 | 12/2006 | Lambrecht et al. |
| 7,150,750 B2 | 12/2006 | Damarati |
| 7,163,561 B2 | 1/2007 | Michelson |
| 7,172,627 B2 | 2/2007 | Fiere et al. |
| 7,182,782 B2 | 2/2007 | Kirschman |
| 7,189,199 B2 | 3/2007 | McCarthy et al. |
| 7,189,235 B2 | 3/2007 | Cauthen |
| 7,198,047 B2 | 4/2007 | Lambrecht et al. |
| 7,201,776 B2 | 4/2007 | Ferree et al. |
| 7,214,245 B1 | 5/2007 | Marcolongo et al. |
| 7,220,281 B2 | 5/2007 | Lambrecht et al. |
| 7,223,289 B2 | 5/2007 | Trieu et al. |
| 7,232,463 B2 | 6/2007 | Falahee |
| 7,237,497 B2 | 7/2007 | Johnston |
| 7,258,700 B2 | 8/2007 | Lambrecht et al. |
| 7,273,497 B2 | 9/2007 | Ferree et al. |
| 7,285,121 B2 | 10/2007 | Braun et al. |
| 7,297,146 B2 | 11/2007 | Braun et al. |
| 7,318,840 B2 | 1/2008 | McKay |
| 7,326,249 B2 | 2/2008 | Lange |
| 7,331,956 B2 | 2/2008 | Hovda et al. |
| 7,335,213 B1 | 2/2008 | Hyde et al. |
| RE40,156 E | 3/2008 | Sharps et al. |
| 7,344,539 B2 | 3/2008 | Serhan et al. |
| 7,351,262 B2 | 4/2008 | Bindseil et al. |
| 7,354,452 B2 | 4/2008 | Foley |
| 7,354,453 B2 | 4/2008 | McAfee |
| 7,357,798 B2 | 4/2008 | Sharps et al. |
| 7,361,193 B2 | 4/2008 | Frey et al. |
| 7,396,365 B2 | 7/2008 | Michelson |
| 7,435,260 B2 | 10/2008 | Ferree |
| 7,445,634 B2 | 11/2008 | Trieu |
| 7,465,318 B2 | 12/2008 | Sennett et al. |
| 7,491,179 B2 | 2/2009 | Roy et al. |
| 7,491,236 B2 | 2/2009 | Cragg et al. |
| 7,500,978 B2 | 3/2009 | Gorensek et al. |
| 7,503,936 B2 | 3/2009 | Trieu |
| 7,507,243 B2 | 3/2009 | Lambrecht et al. |
| 7,513,911 B2 | 4/2009 | Lambrecht et al. |
| 7,524,333 B2 | 4/2009 | Lambrecht et al. |
| 7,534,267 B2 | 5/2009 | Eckman |
| 7,534,268 B2 | 5/2009 | Hudgins et al. |
| 7,547,326 B2 | 6/2009 | Bhatnagar et al. |
| 7,553,329 B2 | 6/2009 | Lambrecht et al. |
| 7,553,330 B2 | 6/2009 | Lambrecht et al. |
| 7,563,282 B2 | 7/2009 | Lambrecht et al. |
| 7,575,577 B2 | 8/2009 | Boyd et al. |
| 7,578,835 B2 | 8/2009 | Wang et al. |
| 7,579,322 B2 | 8/2009 | Akella et al. |
| 7,601,157 B2 | 10/2009 | Boyd et al. |
| 7,601,172 B2 | 10/2009 | Segal et al. |
| 7,608,108 B2 | 10/2009 | Bhatnagar et al. |
| 7,611,536 B2 | 11/2009 | Michelson |
| 7,615,076 B2 | 11/2009 | Cauthen et al. |
| 7,618,461 B2 | 11/2009 | Trieu |
| 7,632,313 B2 | 12/2009 | Bhatnagar et al. |
| 7,637,951 B2 | 12/2009 | Michelson |
| 7,658,765 B2 | 2/2010 | Lambrecht et al. |
| 7,666,205 B2 | 2/2010 | Weikel et al. |
| 7,670,379 B2 | 3/2010 | Cauthen |
| 7,670,380 B2 | 3/2010 | Cauthen, III |
| 7,682,392 B2 | 3/2010 | Serhan et al. |
| 7,682,393 B2 | 3/2010 | Trieu et al. |
| 7,695,425 B2 | 4/2010 | Schweich et al. |
| 7,708,733 B2 | 5/2010 | Sanders et al. |
| 7,713,301 B2 | 5/2010 | Bao et al. |
| 7,717,961 B2 | 5/2010 | Lambrecht et al. |
| 7,722,523 B2 | 5/2010 | Mortier et al. |
| 7,727,241 B2 | 6/2010 | Gorensek et al. |
| 7,740,659 B2 | 6/2010 | Zarda et al. |
| 7,740,660 B2 | 6/2010 | Collins et al. |
| 7,749,230 B2 | 7/2010 | Yuan et al. |
| 7,749,273 B2 | 7/2010 | Cauthen et al. |
| 7,749,275 B2 | 7/2010 | Lambrecht et al. |
| 7,753,941 B2 | 7/2010 | Keith et al. |
| 7,763,051 B2 | 7/2010 | Labrom et al. |
| 7,763,077 B2 | 7/2010 | Friedman et al. |
| 7,766,812 B2 | 8/2010 | Schroeder et al. |
| 7,766,965 B2 | 8/2010 | Bao et al. |
| 7,776,096 B2 | 8/2010 | Cauthen |
| 7,799,060 B2 | 9/2010 | Lange et al. |
| 7,803,188 B2 | 9/2010 | Justis et al. |
| 7,828,850 B2 | 11/2010 | Cauthen, III et al. |
| 7,833,251 B1 | 11/2010 | Ahlgren et al. |
| 7,837,733 B2 | 11/2010 | Collins et al. |
| 7,857,855 B2 | 12/2010 | Ferree |
| 7,857,857 B2 | 12/2010 | Kim |
| 7,867,278 B2 | 1/2011 | Lambrecht et al. |
| 7,879,097 B2 | 2/2011 | Lambrecht et al. |
| 7,905,885 B2 | 3/2011 | Johnson et al. |
| 7,909,879 B2 | 3/2011 | Cauthen |
| 7,922,768 B2 | 4/2011 | Cauthen et al. |
| 7,931,679 B2 | 4/2011 | Heggeness et al. |
| 7,931,689 B2 | 4/2011 | Hochschuler et al. |
| 7,935,147 B2 | 5/2011 | Wales |
| 7,935,149 B2 | 5/2011 | Michelson |
| 7,942,928 B2 | 5/2011 | Webler et al. |
| 7,946,236 B2 | 5/2011 | Butcher |
| 7,951,201 B2 | 5/2011 | Cauthen et al. |
| 7,959,676 B2 | 6/2011 | Thramann et al. |
| 7,959,679 B2 | 6/2011 | Lambrecht |
| 7,959,683 B2 | 6/2011 | Semler et al. |
| 7,967,864 B2 | 6/2011 | Schaller et al. |
| 7,972,337 B2 | 7/2011 | Boyajian et al. |
| 7,972,363 B2 | 7/2011 | Moskowitz et al. |
| 7,993,402 B2 | 8/2011 | Sidler |
| 7,998,213 B2 | 8/2011 | Lambrecht et al. |
| 8,002,836 B2 | 8/2011 | Lambrecht |
| 8,012,211 B2 | 9/2011 | Kuslich |
| 8,021,425 B2 | 9/2011 | Lambrecht et al. |
| 8,025,698 B2 | 9/2011 | Lambrecht et al. |
| 8,034,112 B2 | 10/2011 | Cauthen et al. |
| 8,048,160 B2 | 11/2011 | Cauthen |
| 8,075,618 B2 | 12/2011 | Trieu et al. |
| 8,088,165 B2 | 1/2012 | Cauthen et al. |
| 8,105,384 B2 | 1/2012 | Lambrecht et al. |
| 8,114,082 B2 | 2/2012 | Boyajian et al. |
| 8,128,698 B2 | 3/2012 | Bentley et al. |
| 8,231,678 B2 | 7/2012 | Lambrecht |

(56) References Cited

U.S. PATENT DOCUMENTS

| | | |
|---|---|---|
| 8,257,437 B2 | 9/2012 | Lambrecht et al. |
| 8,323,341 B2 | 12/2012 | Lambrecht et al. |
| 8,361,155 B2 | 1/2013 | Lambrecht et al. |
| 8,394,146 B2 | 3/2013 | Boyajian et al. |
| 8,409,284 B2 | 4/2013 | Lambrecht |
| 8,450,288 B2 | 5/2013 | Boyd |
| 8,454,612 B2 | 6/2013 | Lambrecht et al. |
| 8,454,697 B2 | 6/2013 | Bentley et al. |
| 8,535,338 B2 | 9/2013 | Wales et al. |
| 8,556,977 B2 | 10/2013 | Cauthen et al. |
| 8,632,590 B2 | 1/2014 | Cauthen et al. |
| 9,039,741 B2 | 5/2015 | Lambrecht |
| 9,226,832 B2 | 1/2016 | Lambrecht et al. |
| 9,333,087 B2 | 5/2016 | Lambrecht |
| 2001/0004710 A1 | 6/2001 | Felt et al. |
| 2002/0026244 A1 | 2/2002 | Trieu |
| 2002/0045942 A1 | 4/2002 | Ham |
| 2002/0049498 A1 | 4/2002 | Yuksel et al. |
| 2002/0111688 A1 | 8/2002 | Cauthen |
| 2002/0120270 A1 | 8/2002 | Trieu et al. |
| 2002/0120337 A1 | 8/2002 | Cauthen |
| 2002/0123807 A1 | 9/2002 | Cauthen, III |
| 2002/0133155 A1 | 9/2002 | Ferree |
| 2002/0143329 A1 | 10/2002 | Serhan et al. |
| 2002/0147496 A1 | 10/2002 | Belef et al. |
| 2002/0151980 A1 | 10/2002 | Cauthen |
| 2002/0165542 A1 | 11/2002 | Ferree |
| 2002/0189622 A1 | 12/2002 | Cauthen, III et al. |
| 2002/0198599 A1 | 12/2002 | Haldimann |
| 2003/0004574 A1 | 1/2003 | Ferree |
| 2003/0040796 A1 | 2/2003 | Ferree |
| 2003/0045937 A1 | 3/2003 | Ginn |
| 2003/0050702 A1 | 3/2003 | Berger |
| 2003/0074075 A1 | 4/2003 | Thomas, Jr. et al. |
| 2003/0074076 A1 | 4/2003 | Ferree et al. |
| 2003/0078579 A1 | 4/2003 | Ferree |
| 2003/0130738 A1 | 7/2003 | Hovda et al. |
| 2003/0149438 A1 | 8/2003 | Nichols et al. |
| 2003/0158604 A1 | 8/2003 | Cauthen et al. |
| 2003/0195514 A1 | 10/2003 | Trieu et al. |
| 2004/0002764 A1 | 1/2004 | Gainor et al. |
| 2004/0010317 A1 | 1/2004 | Lambrecht et al. |
| 2004/0024465 A1 | 2/2004 | Lambrecht et al. |
| 2004/0034353 A1 | 2/2004 | Michelson |
| 2004/0044412 A1 | 3/2004 | Lambrecht et al. |
| 2004/0097927 A1 | 5/2004 | Yeung et al. |
| 2004/0097980 A1 | 5/2004 | Ferree |
| 2004/0116922 A1 | 6/2004 | Hovda et al. |
| 2004/0138673 A1 | 7/2004 | Lambrecht et al. |
| 2004/0249464 A1 | 12/2004 | Bindseil et al. |
| 2004/0260238 A1 | 12/2004 | Call |
| 2004/0260300 A1 | 12/2004 | Gorensek et al. |
| 2004/0260397 A1 | 12/2004 | Lambrecht et al. |
| 2005/0010205 A1 | 1/2005 | Hovda et al. |
| 2005/0015148 A1 | 1/2005 | Jansen et al. |
| 2005/0027362 A1 | 2/2005 | Williams et al. |
| 2005/0033440 A1 | 2/2005 | Lambrecht et al. |
| 2005/0060038 A1 | 3/2005 | Lambrecht et al. |
| 2005/0143825 A1 | 6/2005 | Enayati |
| 2005/0206039 A1 | 9/2005 | Lambrecht et al. |
| 2005/0278023 A1 | 12/2005 | Zwirkoski |
| 2006/0030857 A1 | 2/2006 | de Villiers et al. |
| 2006/0030884 A1 | 2/2006 | Yeung et al. |
| 2006/0052874 A1 | 3/2006 | Johnson et al. |
| 2006/0085081 A1 | 4/2006 | Shadduck et al. |
| 2006/0089717 A1 | 4/2006 | Krishna et al. |
| 2006/0100304 A1 | 5/2006 | Vresilovic et al. |
| 2006/0106461 A1 | 5/2006 | Embry et al. |
| 2006/0129156 A1 | 6/2006 | Cauthen et al. |
| 2006/0161162 A1 | 7/2006 | Lambrecht et al. |
| 2006/0184246 A1 | 8/2006 | Zwirkoski |
| 2006/0200246 A1 | 9/2006 | Lambrecht et al. |
| 2006/0217747 A1 | 9/2006 | Ferree |
| 2006/0253121 A1 | 11/2006 | Gorensek et al. |
| 2006/0265077 A1 | 11/2006 | Zwirkoski |
| 2007/0027471 A1 | 2/2007 | Ferree |
| 2007/0055375 A1 | 3/2007 | Ferree |
| 2007/0061012 A1 | 3/2007 | Cauthen, III |
| 2007/0067039 A1 | 3/2007 | Lambrecbt et al. |
| 2007/0093822 A1 | 4/2007 | Dutoit et al. |
| 2007/0093912 A1 | 4/2007 | Borden |
| 2007/0118133 A1 | 5/2007 | Lambrecht et al. |
| 2007/0118226 A1 | 5/2007 | Lambrecht et al. |
| 2007/0135920 A1 | 6/2007 | Ferree |
| 2007/0142839 A1 | 6/2007 | Ferree |
| 2007/0156152 A1 | 7/2007 | Ferree |
| 2007/0156244 A1 | 7/2007 | Cauthen |
| 2007/0162132 A1 | 7/2007 | Messerli |
| 2007/0179623 A1 | 8/2007 | Trieu et al. |
| 2007/0185497 A1 | 8/2007 | Cauthen et al. |
| 2007/0198021 A1 | 8/2007 | Wales |
| 2007/0233146 A1 | 10/2007 | Henniges et al. |
| 2007/0239278 A1 | 10/2007 | Heinz |
| 2007/0260249 A1 | 11/2007 | Boyajian et al. |
| 2007/0276494 A1 | 11/2007 | Ferree |
| 2008/0009792 A1 | 1/2008 | Henniges et al. |
| 2008/0015693 A1 | 1/2008 | Le Couedic |
| 2008/0039586 A1 | 2/2008 | Hasenwinkel et al. |
| 2008/0051800 A1 | 2/2008 | Diaz et al. |
| 2008/0082172 A1 | 4/2008 | Jackson |
| 2008/0140126 A1 | 6/2008 | Ferree |
| 2008/0172058 A1 | 7/2008 | Trieu et al. |
| 2008/0195119 A1 | 8/2008 | Ferree |
| 2008/0221686 A1 | 9/2008 | Ferree |
| 2008/0243256 A1 | 10/2008 | Ferree |
| 2008/0269898 A1 | 10/2008 | Carls et al. |
| 2009/0012540 A1 | 1/2009 | Ferguson et al. |
| 2009/0024165 A1 | 1/2009 | Ferree |
| 2009/0118833 A1 | 5/2009 | Hudgins et al. |
| 2009/0143862 A1 | 6/2009 | Trieu |
| 2009/0157087 A1 | 6/2009 | Wei et al. |
| 2009/0187249 A1 | 7/2009 | Osman |
| 2009/0204216 A1 | 8/2009 | Biedermann et al. |
| 2009/0204220 A1 | 8/2009 | Trieu |
| 2009/0222093 A1 | 9/2009 | Liu et al. |
| 2009/0234457 A1 | 9/2009 | Lotz et al. |
| 2009/0270989 A1 | 10/2009 | Conner et al. |
| 2009/0270990 A1 | 10/2009 | Louis et al. |
| 2009/0275913 A1 | 11/2009 | Trieu |
| 2009/0281517 A1 | 11/2009 | Lambrecht et al. |
| 2009/0292322 A1 | 11/2009 | Lambrecht |
| 2010/0004664 A1 | 1/2010 | Boyajian et al. |
| 2010/0030333 A1 | 2/2010 | Michelson |
| 2010/0049259 A1 | 2/2010 | Lambrecht et al. |
| 2010/0057143 A1 | 3/2010 | Lambrecht et al. |
| 2010/0087926 A1 | 4/2010 | Butler et al. |
| 2010/0094425 A1 | 4/2010 | Bentley et al. |
| 2010/0114317 A1 | 5/2010 | Lambrecht et al. |
| 2010/0121455 A1 | 5/2010 | Lambrecht et al. |
| 2010/0145454 A1 | 6/2010 | Hoffman |
| 2010/0145463 A1 | 6/2010 | Michelson |
| 2010/0152784 A1 | 6/2010 | Lowry et al. |
| 2010/0152790 A1 | 6/2010 | Hestad |
| 2010/0161056 A1 | 6/2010 | Voellmicke et al. |
| 2010/0161060 A1 | 6/2010 | Schaller et al. |
| 2010/0185285 A1 | 7/2010 | Perkins |
| 2010/0185286 A1 | 7/2010 | Allard et al. |
| 2010/0191335 A1 | 7/2010 | Root et al. |
| 2010/0204797 A1 | 8/2010 | Lambrecht |
| 2010/0211108 A1 | 8/2010 | Lemole |
| 2010/0298837 A1 | 11/2010 | Gorensek |
| 2011/0022061 A1 | 1/2011 | Orphanos et al. |
| 2011/0106264 A1 | 5/2011 | Lambrecht et al. |
| 2011/0118844 A1 | 5/2011 | Lambrecht |
| 2011/0196492 A1 | 8/2011 | Lambrecht et al. |
| 2011/0264227 A1 | 10/2011 | Boyajian et al. |
| 2012/0289865 A1 | 11/2012 | Lambrecht et al. |
| 2012/0316648 A1 | 12/2012 | Lambrecht et al. |
| 2013/0184750 A1 | 7/2013 | Lambrecht et al. |
| 2013/0204373 A1 | 8/2013 | Lambrecht et al. |
| 2014/0005786 A1 | 1/2014 | Lambrecht et al. |
| 2016/0184110 A1 | 6/2016 | Lambrecht et al. |

(56) References Cited

U.S. PATENT DOCUMENTS

FOREIGN PATENT DOCUMENTS

| | | |
|---|---|---|
| EP | 0298235 | 1/1989 |
| EP | 0682910 | 3/1995 |
| EP | 0700671 | 3/1996 |
| EP | 0876808 | 11/1998 |
| EP | 0722700 | 12/1998 |
| EP | 1091776 | 5/2004 |
| EP | 1214026 | 4/2005 |
| EP | 1180978 | 5/2005 |
| FR | 2639823 A1 | 6/1990 |
| FR | 2668921 | 5/1992 |
| JP | S64-887 | 1/1989 |
| JP | H05-29694 | 7/1993 |
| JP | 1995-148172 | 6/1995 |
| JP | S63-95043 | 4/1998 |
| RU | 2020901 | 10/1994 |
| RU | 93031998 A | 11/1995 |
| RU | 2055544 | 3/1996 |
| RU | 2078551 | 5/1997 |
| RU | 96121354 A | 1/1999 |
| SU | 1710007 | 2/1992 |
| WO | WO 92/10982 | 9/1992 |
| WO | WO 93/22990 | 11/1993 |
| WO | WO 95/26689 | 10/1995 |
| WO | WO 95/31946 | 11/1995 |
| WO | WO 95/34331 | 12/1995 |
| WO | WO 96/01164 | 1/1996 |
| WO | WO 96/01598 | 1/1996 |
| WO | WO 97/26847 | 7/1997 |
| WO | WO 97/30638 | 8/1997 |
| WO | WO 98/17190 | 4/1998 |
| WO | WO 98/20939 | 5/1998 |
| WO | WO 98/34552 | 8/1998 |
| WO | WO 98/38918 | 9/1998 |
| WO | WO 99/00074 | 1/1999 |
| WO | WO 99/02108 | 1/1999 |
| WO | WO 99/02214 | 1/1999 |
| WO | WO 99/03422 | 1/1999 |
| WO | WO 99/30651 | 6/1999 |
| WO | WO 99/47058 | 9/1999 |
| WO | WO 99/61084 | 9/1999 |
| WO | WO 99/62439 | 12/1999 |
| WO | WO 00/14708 | 3/2000 |
| WO | WO 00/18328 | 4/2000 |
| WO | WO 00/42953 | 7/2000 |
| WO | WO 00/44288 | 8/2000 |
| WO | WO 00/45741 | 8/2000 |
| WO | WO 00/49978 | 8/2000 |
| WO | WO 00/62832 | 10/2000 |
| WO | WO 00/71043 | 11/2000 |
| WO | WO 01/10316 | 2/2001 |
| WO | WO 01/12080 | 2/2001 |
| WO | WO 01/12107 | 2/2001 |
| WO | WO 01/21246 | 3/2001 |
| WO | WO 01/28464 | 4/2001 |
| WO | WO 01/28468 | 4/2001 |
| WO | WO 01/39696 | 6/2001 |
| WO | WO 01/45579 | 6/2001 |
| WO | WO 01/52914 | 7/2001 |
| WO | WO 01/78616 | 10/2001 |
| WO | WO 01/45577 | 6/2002 |
| WO | WO 02/051622 | 7/2002 |
| WO | WO 02/058599 | 8/2002 |
| WO | WO 02/067824 | 9/2002 |
| WO | WO 03/039328 | 5/2003 |
| WO | WO 03/088876 | 10/2003 |
| WO | WO2004/080355 | 9/2004 |
| WO | WO2005/027800 | 3/2005 |

OTHER PUBLICATIONS

Bagga C.S., Williams P., Highma P.A., Bao B.Q., "Development of Fatigue Test Model for a Spinal Nucleus Prosthesis with Preliminary Results for a Hydrogel Spinal Prosthetic Nucleus," Proceedings of the 1997 Bioengineering Conference, 441-442: BED-vol. 35, Sunriver, Oregon, Jun. 11-15, 1997.

Balderston, R.A., et al., "The Treatment of Lumbar Disc Herniation: Simple Fragment Excision Versus Disc Space Curettage," *J. of Spinal Disorders*, 4 (1) : 22-25 (1991).

Bao Q.B., Bagga C.S., "The Dynamic Mechanical Analysis of Hydrogel Elastomers," Thermochimica Acta, 226:107-113 (1993).

Bao Q.B., McCullen G.M., Higham P.A., Dumbleton J.H., Yuan H.A., "The Artificial Disc: Theory, Design and Materials," Biomaterials, vol. 17, No. 12:1157-1167 (1996).

Bao Q.B., Yuan H.A., "Artificial Disc Technology," Neurosurg Focus 9(4), 2000.

Barr, J.S., "Ruptured Intervertebral Disc and Sciatic Pain," *J. of Bone and Joint Surgery*, 29, (2) : 429-437 (1947).

Brinckmann, P., et al., "Change of Disc Height, Radial Disc Bulge, and Intradiscal Pressure From Discectomy An in Vitro Investigation on Human Lumbar Discs," *Spine*, 16 (6) : 641-646 (1991).

Cauthen, Joseph, Draft Abstract entitled *Microsurgical Annular Reconstruction (Annuloplasty) Following Lumbar Microdiscectomy: Preliminary Report of a New Technique*, from abstracts@neurosurgery.org, reportedly published in Feb. 1999 and dated Sep. 4, 1998, and contextual documents, 39 pages.

Goel, V.K., et al., "Mechanical Properties of Lumbar Spinal Motion Segments as Affected by Partial Disc Removal," *Spine*, 11 (10) : 1008-1012 (1986).

Hanley, E.N., Jr., et al., "The Development of Low-Back Pain After Excision of a Lumbar Disc," *J. of Bone and Joint Surgery*, 71A (5) : 719-721 (1989).

Hedman T.P., Kostuik J.P., Fernie G.R., Hellier W.G., "Design of an Intervertebral Disc Prosthesis," Spine 16 (Suppl. 6):5256-5260 (1991).

Heggeness, M.H., et al., "Discography of Lumbar Discs After Surgical Treatment for Disc Herniation," *Spine*, 22 (14) : 1606-1609 (1997).

Husson J.L., Baumgartner W., Le Huec J.C., "Nucléoplastie Inter-Somatique Par Voie Postérieure Per-Dissectomie: Concept et Étude Expérimentale," Restabilisation Inter-Somatique Due Rachis Lombaire:311-320 (1996).

Husson J.L., Scharer N., Le Nihouannen J.C., Freudiger S., Baumgartner W., Polard J.L., "Nucleoplasty During Discectomy Concept and Experimental Study," Rachis vol. 9, No. 3:145-152 (1997).

Kayama, S., et al., "Incision of the Anulus Fibrosus Induces Nerve Root Morphologic, Vascular, and Functional Changes," *Spine*, 21 (22) : 2539-2543 (1996).

Khelimsky et al. "Plastic Surgery of Damaged Intervertebral Discs with Fast-Solidifying Glue Composition (Experimental Research)." Collected articles Experimental Traumatic Surgery and Orthopaedics Moscow, 1990, pp. 88-90.

Langrana N.A., Parsons J.R., Lee C.K., Vuono-Hawkins M., Yang S.W., Alexander H., "Materials and Design Concepts for an Intervertebral Disc Spacer. I. Fiber-Reinforced Composite Design," Journal of Applied Biomaterials, vol. 4:125-132 (1994).

Lemaire J.P., Skalli W., Lavaste F., Templier A., Mendes, F., Diop A., Sauty V., Laloux E., "Intervertebral Disc Prosthesis," Clinical Orthopaedics and Related Research, No. 337:64-76 (1997).

Martz E.O., Goel V.K., Pope M.H., Park J.B., "Materials and Design of Spinal Implants—A Review," Journal of Biomedical Materials Research, vol. 38, Issue 3:267-288 (1997).

Postacchini, F., "Spine Update results of Surgery Compared With Conservative Management for Lumbar Disc Herniations," *Spine*, 21 (11) : 1383-1387 (1996).

Ray C.D., Schonmayr R., Kavanagh S.A., Assell R., "Prosthetic Disc Nucleus Implants," Riv. Neuroradiol 1999:12 (Suppl. 1):157-162.

Rogers, L.A., "Experience with Limited versus Extensive Disc Removal in Patients Undergoing Microsurgical Operations for Ruptured Lumbar Discs," *Neurosurgery*, 22 (1) : 82-85 (1988).

Sakalkale D.P., Bhagia S.A., Slipman C.W., "A Historical Review and Current Perspective on the Intervertebral Disc Prosthesis," Pain Physician, vol. 6, No. 2:1-4 (2003).

(56) References Cited

OTHER PUBLICATIONS

Schonmayr R., Busch C., Lotz C., Lotz-Metz G., "Prosthetic Disc Nucleus Implants: The Wiesbaden Feasibility Study, 2 Years follow-up in Ten patients," Riv. Neuroradiol 1999:12 (Suppl. 1):163-170.
Sheljakin S. Ju. "Percutaneous Diskectomy Skin-through Discectomy in Complex Treatment of Patients with Disc Lumbosacral Polyraduculitis." Abstract of a thesis, St. Petersburg, 1996.
Shul'man Kh.M. "Pathogenetic Therapy of Compression Type Osteochondritis of Spinal Lumbar Region." Collected articles Reconstruction-and-Restoration Treatment in Traumatic Surgery, Orthopaedics, Surgery and Neurosurgery, Kazan', 1976, pp. 17-21.
Shul'man Kh.M. "Surgical Treatment of Compression Type Osteochondritis of Spinal Lumbar Region with Intervertebral Disc Implantation." Kazan', 1980, pp. 174-185.
Shul'man Kh.M., Danilov V.I. "Biochemical Experimental Basis of Intervertebral Disc Prosthesis Implantation Method by Fast-solidifying Polyurethane CKYu-PFL in Case of Disc Degeneration or Traumatic Damage." Collected articles Reconstruction-and-Restoration Treatment in Traumatic Surgery, Orthopaedics, Surgery and Neurosurgery. Kazan', 1976, pp. 22-27.

Tibrewal, S.B., et al., "Lumbar Intervertebral Disc Heights in Normal Subjects and Patients with Disc Herniation," *Spine*, 10 (5) : 452-454 (1985).
Tullberg, T., et al., "Radiographic Changes After Lumbar Discectomy," *Spine*, 18 (7) : 843-850 (1993).
Usmanov M.M. "Intervertebral Disc Changes at Local Damage of its Elements and Implantation of Various Materials." Abstract of a thesis Moscow, 1991.
USSR Author's Certificate No. 1477390 "Method for Treatment of Osteochondritis." Published May 17, 1989.
USSR Author's Certificate No. 1827204 "Method for Treatment of Spinal Osteochondritis." Published May 15, 1993.
Yasargil, M.G., Microsurgical Operation of Herniated Lumbar Disc, Adv. Neurosurg 1977;4:81.
Zelentsov E.V. "Plastic Surgery with Collagen of Intervertebral Discs for Surgical Treatment of Lumbosacral Polyradiculitis." Abstract of a thesis, Leningrad, 1990.
Zelentsov E.V. et al. "Application of Collagen for Experimental Plastic Surgery of Intervertebral Discs." Collected articles Integrated Treating of Pain Syndromes of Neurogenic Origin, Leningrad 1984 pp. 86-90.

* cited by examiner

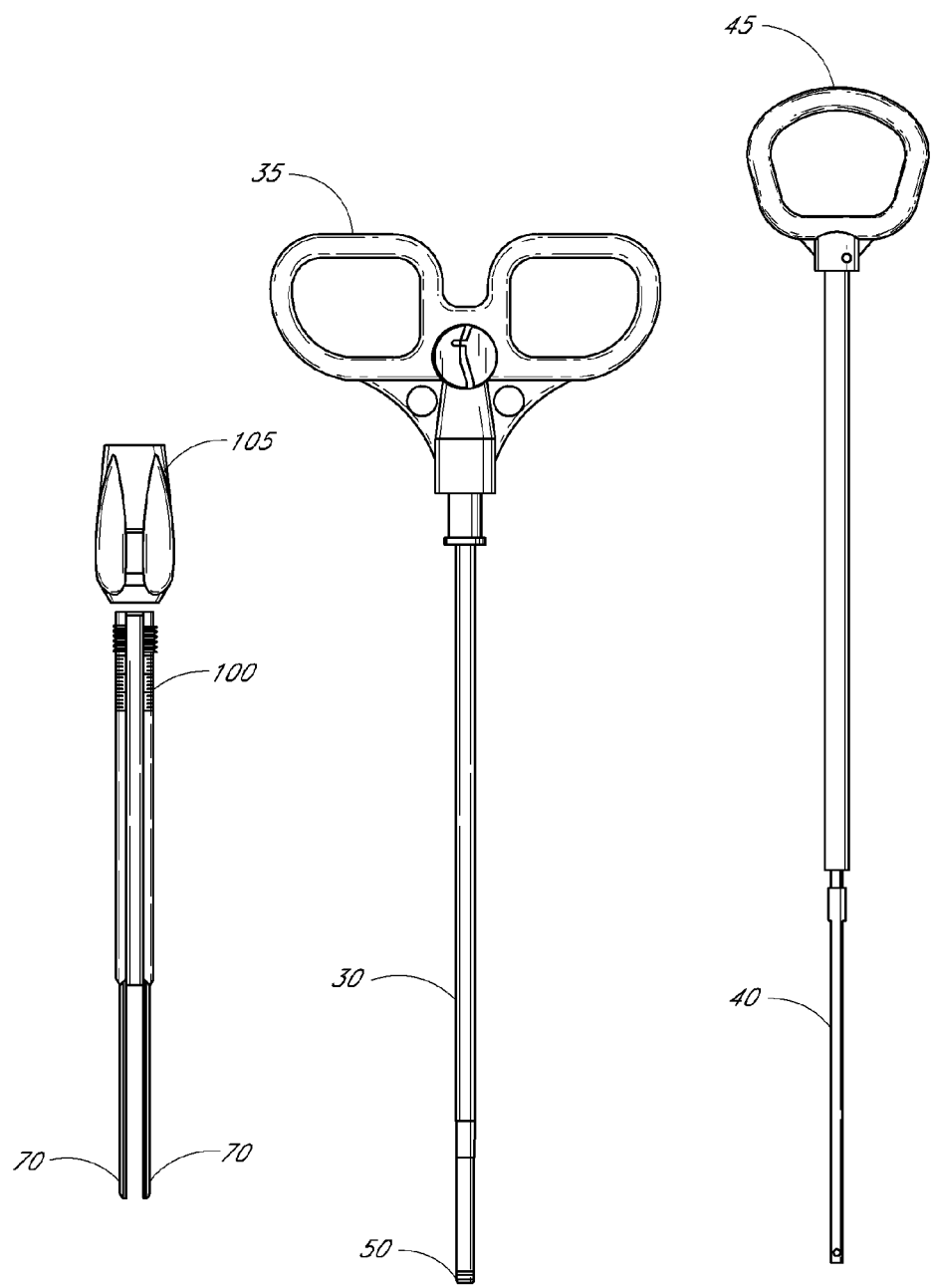
*FIG. 4*   *FIG. 5*   *FIG. 6*

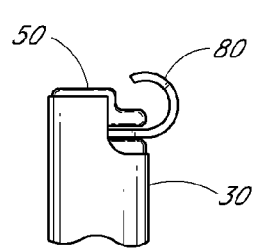 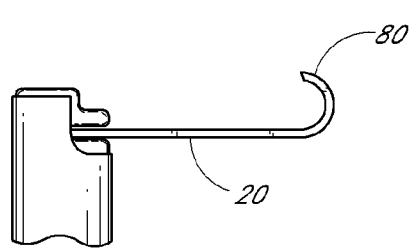 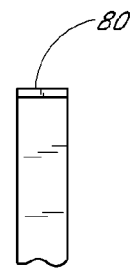
*FIG. 11A*   *FIG. 11B*   *FIG. 12*
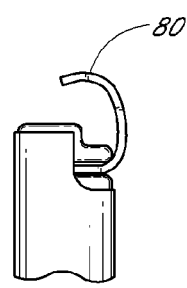 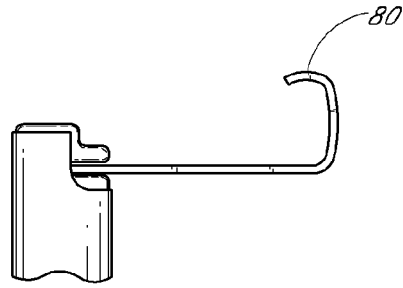 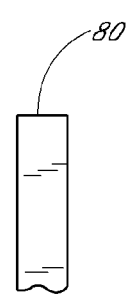
*FIG. 13A*   *FIG. 13B*   *FIG. 14*
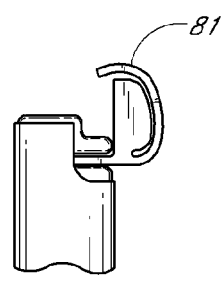 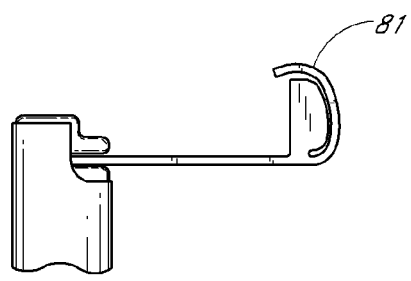 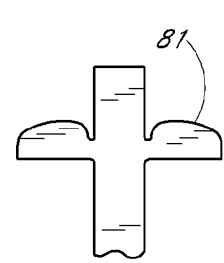
*FIG. 15A*   *FIG. 15B*   *FIG. 16*

METHOD OF PERFORMING AN ANCHOR IMPLANTATION PROCEDURE WITHIN A DISC

RELATED APPLICATIONS

This application is a continuation of U.S. application Ser. No. 11/417,793, filed May 3, 2006, which is a continuation of U.S. application Ser. No. 10/359,516, filed Feb. 5, 2003, now issued as U.S. Pat. No. 7,717,961, which is a continuation-in-part of U.S. application Ser. No. 10/020,507, filed Dec. 11, 2001, now issued as U.S. Pat. No. 6,821,276, which claims benefit to U.S. Provisional Application No. 60/298,605, filed Jun. 14, 2001, and wherein 10/359,516 is a continuation-in-part of U.S. application Ser. No. 10/055,504, filed Oct. 25, 2001, now issued as U.S. Pat. No. 7,258,700, which claims benefit to U.S. Provisional Application No. 60/311,586, filed Aug. 10, 2001, and wherein 10/359,516 is a continuation-in-part of U.S. application Ser. No. 10/325,320, filed Dec. 19, 2002, now issued as U.S. Pat. No. 7,124,761, which is a continuation of U.S. application Ser. No. 09/696,636, filed Oct. 25, 2000, now issued as U.S. Pat. No. 6,508,839, which is a continuation-in-part of U.S. application Ser. No. 09/642,450, filed Aug. 18, 2000, now issued as U.S. Pat. No. 6,482,235, which is a continuation-in-part of U.S. application Ser. No. 09/608,797, filed Jun. 30, 2000, now issued as U.S. Pat. No. 6,425,919, which claims benefit to U.S. Provisional Application No. 60/172,996, filed Dec. 21, 1999, U.S. Provisional Application No. 60/161,085, filed Oct. 25, 1999, and U.S. Provisional Application No. 60/149,490 filed Aug. 18, 1999, all of which are incorporated by reference herein.

BACKGROUND

Field

The present invention relates generally to devices and instrumentation for intervertebral disc diagnosis and treatment, and methods thereof.

Description of the Related Art

An intervertebral disc performs the important role of absorbing mechanical loads while allowing for constrained flexibility of the spine. The disc is composed of a soft, central nucleus pulposus surrounded by a tough, woven anulus fibrosus. Herniation is a result of a weakening in the anulus. Symptomatic herniations occur when weakness in the anulus allows the nucleus to bulge or leak posteriorly toward the spinal cord and major nerve roots. The most common symptoms of herniation include pain radiating along a compressed nerve and lower back pain, both of which can be crippling for the patient. Herniation, and the resulting dehabilitating symptoms, are of significant medical concern in the United States because of the low average age of diagnosis. Indeed, over 80% of patients in the United States diagnosed with herniation are under the age of 59.

Information regarding anular thickness, internal dimensions of the disc space normally occupied by the nucleus, and the location of anular apertures and lesions in relation to the vertebral endplates and lateral walls of the anulus facilitates accurate diagnosis and treatment of intervertebral disc conditions. For example, medical procedures involving the implantation of an artificial nucleus or anular augmentation depend on this information for accurate sizing of such implants. Also important are safe, dependable, and minimally invasive methods and devices for the manipulation of anular and nuclear tissue, especially along the inner wall of the posterior anulus. For example, tissues in the anulus and nucleus are commonly removed or manipulated during the implantation of artificial discs either to clear a path for the insertion of other types of prosthetic devices or as part of a discectomy procedure.

Specialized tools have evolved for the surgical treatment of intervertebral discs in the lumbar, cervical, and thoracic spine, which have suffered from tears in the anulus fibrosis or herniation of the nucleus pulposus. These tools are well-known in the prior art. The devices of the prior art, however, are designed for specific procedures, including complete discectomies (as opposed to partial discectomy or minute removal of tissue) and the installation of vertebral fusion implants. Accordingly, these devices cannot be used to manipulate anular and nuclear tissue in a precise and minimally invasive manner. Moreover, such devices are typically designed to access the disc using an anterior approach, i.e., through the abdomen. Although an anterior surgical approach provides direct access to intervertebral discs, it is highly invasive to the abdominal organs. Thus, surgery is typically more complicated and time consuming. A direct posterior approach is not anatomically practicable because the spinal cord and its surrounding bony protective sheath lies directly in front of each vertebral disc. An posterior-lateral aspect approach is the least invasive of these methods but provides limited and oblique access to the disc and its interior. Depending upon the surgical necessities involved, several methods of percutaneous disc tissue manipulation are available, including chemonucleolysis (e.g., U.S. Pat. No. 4,439,423), laser (e.g., U.S. Pat. No. 5,437,661), manual, focused energy, ultrasonic disruption (e.g., U.S. Pat. No. 5,772,661), arthroscopy and endoscopy.

Endoscopic instrumentation has evolved over the past 25 years and permits viewing, irrigation, suction, and cutting. Probes that permit automated percutaneous suction such as nucleotomes or cylindrically housed rotating cutting means, such as debriders, provide gross but efficient removal of disc tissue. Varying tip profiles control the amount and direction of tissue resection as well as the likelihood of damage to surrounding tissue. These devices tend to be limited by the size of the cannula which houses the instrumentation and its ability to maneuver around vertebral bodies and delicate tissues of the spine.

Hand tools for use in the spine are also well known and can be inserted through cannulae or freely guided by hand. These tips may be blades, burs, rongeurs, curettes or forcep-like "graspers" that are capable of pinching of small amounts of material. To the extent that these instruments can access the various tissues, these devices provide good tactical feedback and control. However, if used in an antero-lateral spinal approach, these tools are generally limited by the indirect approach necessitated by the laminae and spinous processes of the adjacent vertebrae, and thus, access to tissues is substantially hampered.

Some intervertebral disc devices have been designed with flexible tips that are designed not to perforate or deflect off of the interior surface of the disc. Unfortunately, such tips deflect off of healthy disc tissue only, not the pathological tissue that caused the need for the surgery in the first place. Thus, such instrumentation can exit the anulus and cause considerable damage to the surrounding tissues and spinal cord. Also, the flexible probe tips on some instruments which permit access to remote locations within the disc can only do so by sacrificing direct control because the devices are passively guided or blindly "snaked" within the disc. Accordingly, delicate and precise work within a disc is not possible with such instruments.

Among other disadvantages, the devices and methods of the prior art are typically invasive and destructive to surrounding tissue, frequently causing disc infection and nerve root injury. Moreover, such devices are unable to precisely manipulate disc material along the posterior anulus in a minimally invasive manner. Accordingly, there is a need for an intervertebral disc diagnostic and manipulation device which is capable of performing delicate and precise work within a disc, especially along the posterior anulus and between anular lamella.

SUMMARY

Embodiments of current invention relate generally to devices and instrumentation for intervertebral disc diagnosis and treatment, and methods thereof. In several embodiments, the present invention provides for minimally invasive and actively guided intervertebral diagnostic and implant delivery devices.

Various embodiments of the disclosed devices may be guided by tactile feedback or through active viewing. Also, various embodiments may be used in conjunction with medical imaging technologies, including MRI, ultrasound, or fluoroscopy. Further, several embodiments of the invention having radiopacity or selective radiopacity may be used in conjunction with imaging methods for guidance and/or to facilitate measurement of organs or tissues.

Various embodiments of the disclosed devices may be guided by using one or more indicators. These indicators include, but are not limited to, biochemical marker, pH value, tissue density, tissue reflectance and light absorption. In one embodiment, the indicator is coupled to a transducer. The transducer contacts the disc and any signal changes are interpreted to facilitate guiding.

Various embodiments of the current invention are particularly advantageous because they provide active controlled direction of the working end of the instrument within the anulus or nucleus. Further, several embodiments provide access to the posterior portion of the anulus using a posterior surgical approach. In various embodiments, access to the posterior anulus, via circumferential navigation of the instrument as it is deflected from the lateral, anterior, opposite lateral, and finally to the posterior anulus, is avoided. This is advantageous because circumferential deflection of the working end of the instrument within the anulus can result in the tip of the instrument passing through a fissure in the posterior anular surface and outward to the spinal cord. This can occur because the circumferential navigation from a typical posterior surgical approach eventually directs the tip perpendicular to the posterior anular surface, which may contain lesions large enough to allow protrusion of the tip directly through to the spinal cord.

There is provided in accordance with one aspect of the present invention, a device for treating the spine. The device comprises an elongate guide having a longitudinal axis. An axially moveable actuator is carried by the guide. A probe is movable with the actuator, and a deflection surface is carried by the guide. Axial movement of the actuator causes the probe to advance along the deflection surface and extend away from the guide at an angle to the longitudinal access of the guide.

In one implementation of the invention, the guide comprises an elongate tubular body having at least one lumen extending therethrough. The actuator extends through at least a portion of the guide. The probe may comprise an elongate flexible body, attached to the actuator. The probe may be biased in a nonlinear configuration. In one embodiment, the probe comprises a nickel titanium alloy.

In accordance with another aspect of the present invention, there is provided a method of treating a disc in the spine. The method comprises the steps of advancing a device at least part way through an anulus. A probe is advanced laterally from the device in a first direction along a portion of the anulus.

In one application of the invention, the advancing a probe step comprises advancing the probe in between adjacent (anular lamella) layers of the anulus. In another application of the invention, the advancing a probe step comprises advancing the probe along an interior surface of the anulus, between the anulus and the nucleus. The method may further comprise the step of repositioning the probe and advancing the probe in a second direction along a second portion of the anulus.

In accordance with a further aspect of the present invention, the method additionally comprises the step of introducing media through the delivery device and into the disc. In one application, the media comprises contrast media, to permit fluoroscopic visualization. The media may alternatively or additionally comprise a medication, and/or a nucleus augmentation material. The method may additionally comprise the step of introducing a prosthesis into the disc. The prosthesis may be introduced by proximately retracting a push rod from a lumen in the delivery device, and introducing the prosthesis into the disc through the lumen.

As will be appreciated by those of skill in the art, the present invention, therefore, provides a minimally invasive access pathway into the anulus and/or nucleus of a vertebral disc. The pathway may be utilized to perform any of a wide variety of procedures, including diagnostic and therapeutic procedures, some of which will be identified below.

Several embodiments of this invention provide a new intervertebral disc manipulation and diagnostic device.

One or more embodiments disclosed herein provide a convenient, reliable, and accurate way to measure the anular thickness and the internal dimensions of the disc space normally occupied by the nucleus pulposus.

Several embodiments of this invention provide a device useful in determining various disc dimensions in order to enable a surgeon to size various implants and tools and facilitate their guidance within the disc.

Various embodiments provide for the manipulation through an opening in the anulus. Manipulation includes, but is not limited to, dissection, resection or ablation of disc tissue. The opening may be a single iatrogenic hole, such as an anulotomy, a naturally occurring hole, or a lesion in the anulus.

One or more aspects of the current invention prepare or manipulate disc tissue in preparation for the insertion of an implant or other instruments.

Several embodiments of the present invention diagnose and manipulate disc tissue with minimal invasiveness and risk of unintended passage of the device outside of the posterior anulus in the direction of the spinal cord or other sensitive areas proximal thereto.

Various aspects of this invention permit direct access to the interior aspect of anulus via an anulotomy.

Several embodiments of invention provide an intervertebral disc manipulation and diagnostic device wherein the travel of the working end of the device is parallel to the lamellae of the anulus.

Several embodiments of invention provide a method of delivering an intervertebral disc implant. In one embodiment, the method includes the steps of identifying an interface of a lamella of an anulus fibrosus and a nucleus pulposus, providing an implant delivery tool having a depth stop, a proximal end and a distal end, inserting at least a portion of the delivery tool within the anulus such that the depth stop is placed against an external aspect of a functional spinal unit and the distal end of the delivery tool is inserted to a selected depth relative to the interface, and delivering the implant.

Several embodiments of the present invention provide a method of performing a procedure within an intervertebral disc. In one embodiment, the method includes the following steps: identifying a first depth corresponding to an inner surface of an anulus lamella of a selected intervertebral disc, providing a surgical device comprising a depth stop, a proximal end and a distal end, inserting at least a portion of the device within the anulus along a first axis such that said depth stop is placed against an outer surface of a functional spinal unit and the distal end of the device is inserted to a second depth relative to said first, and performing the procedure.

Several embodiments of the invention include a method of performing a procedure on an intervertebral disc that includes the following steps: providing a therapeutic device comprising a distal intradiscal component located at a distal end of said device, advancing at least a portion of the distal end of the therapeutic device into the disc, retracting at least a portion of the device such that at least a portion of the intradiscal component is placed against an inner surface of an anular lamella, and performing a procedure with the device on the disc.

This disclosure utilizes particular orthopedic references, nomenclature, and conventions. Accordingly, several background figures and descriptions are included to aid in the understanding of the environment under which specific embodiments of the invention may be used. In this description and the following claims, the terms "anterior" and "posterior", "superior" and "inferior" are defined by their standard usage in anatomy, i.e., anterior is a direction toward the front (ventral) side of the body or organ, posterior is a direction toward the back (dorsal) side of the body or organ; superior is upward (toward the head) and inferior is lower (toward the feet).

BRIEF DESCRIPTION OF THE DRAWINGS

FIG. 1A is a view of a transverse section. FIG. 1B is a view of a sagittal section.

FIG. 4 is a side view of the depth stop components of the device including depth-measuring markings, the depth stop adjustment knob, and the depth stop body.

FIG. 5 is a side view of the delivery cannula, cannula handle and intradiscal tip.

FIG. 6 is a side view of the advancer, with a ring-handle.

FIG. 11A is a side view of the intradiscal tip of the device showing a variation of the probe tip. In this variation, the trailing edge of the reverse-curved tip has been sharpened. In FIG. 11B, the same intradiscal tip is shown with the probe advanced from its initial retracted position.

FIG. 12 is a top view of the probe from FIGS. 11A and 11B shown unformed. The probe is shown as it would appear prior to forming, if it were formed from a flat sheet of material, sharpened along one edge.

FIG. 13A is a side view of the intradiscal tip of the device, showing a variation of the probe tip. In this variation, the distal end of the reverse-curved tip is spaced further distally from the distal end of the device than that of the probe depicted in FIGS. 11A-B. In FIG. 13B the same device is shown with the probe advanced from its initial retracted position.

FIG. 14 is a top view of the probe from FIGS. 13A and 13B shown unformed. The reverse curve that forms the distal tip of the probe is shown as it would appear prior to forming, if it were formed from a flat sheet of material.

FIG. 15A is a side view of a variation of the probe tip. In this variation, the tip of the reverse curve has two additional flanges of material on either side of the curve. The combination of tip elements forms a scoop. In FIG. 15B the same device is shown with the probe advanced from its initial retracted position.

FIG. 16 is a top plan view of the probe from FIGS. 15A and 15B shown unformed. The two side flanges and the reverse curve that forms the distal tip of the probe are shown as they would appear prior to forming, if they were formed from a flat sheet of material.

FIG. 21A shows an implant being placed along an inner surface of the anulus fibrosus and FIG. 21B shows an implant being placed between anulus lamellae.

DETAILED DESCRIPTION OF THE PREFERRED EMBODIMENT

Figure 1A:
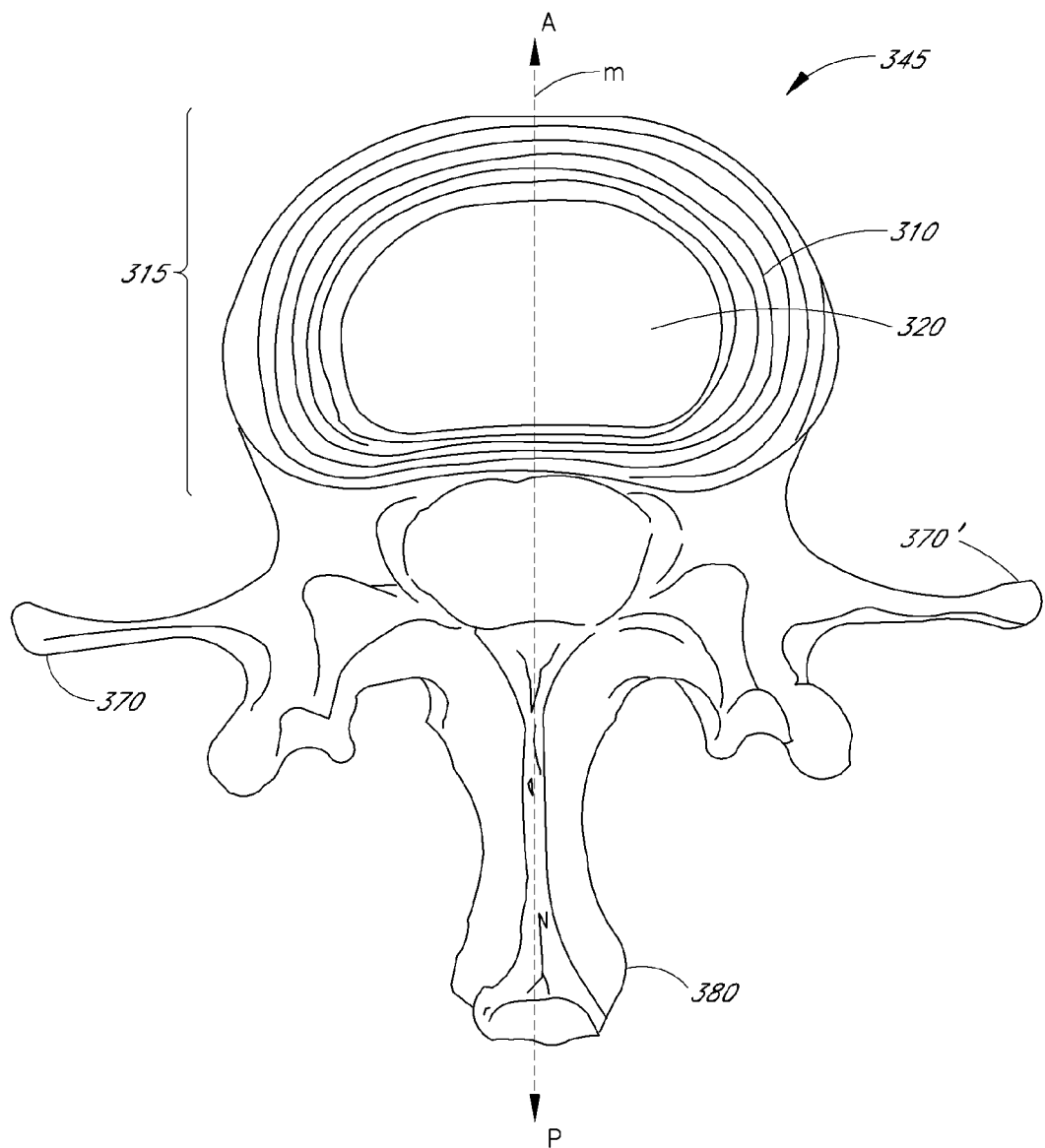
FIGS. 1A and 1B show the general anatomy of a functional spinal unit 345.

In one aspect of the invention, there is provided a guide such as a hollow delivery cannula having a distal end and a proximal end. The guide is dimensioned to fit within a small anulotomy as might be created by a surgeon or through a naturally occurring hole or lesion in the anulus. An advancer, push rod, or actuator is axially moveably carried by the guide, and coupled to a flexible probe member. The flexible probe member has a proximal end connected to the advancer and distal end connected to or formed into a probe tip.

The probe is advanceable outwardly from the distal end of the cannula via axial movement of the advancer within the cannula. In the illustrated embodiment, the probe member exits through a slot having a curved pathway or deflection surface located at the distal end of the cannula and can be advanced outwardly therefrom generally at an angle of between about 30 to about 150 degrees relative to the cannula's longitudinal axis. Accordingly, when the distal end of the cannula is properly inserted within the anulotomy at sufficient depth, the probe travels along a path that is parallel to and along the surface of or in between the anular lamellae. The probe may be retracted via reversing the action (e.g. proximal retraction) of the advancer.

A means for measuring the distance advanced by the probe is associated with the probe and cannula. Any of a variety of measurement indicia may be used, such as calibrated markings on the advancer visible through or proximal to the cannula. An indicator for measuring the distance advanced by the cannula within the anulotomy or lesion may also be included. For example, a calibrated depth stop may be affixed in a slideably adjustable manner to the delivery cannula.

The probe tip at the distal end of the probe member may be an integral piece of the probe wherein the tip and the probe are of a unitary construction. Alternatively, the tip may be secured, either releasably or permanently to the probe. The tip can be blunt enabling it to forcibly part the tissue without cutting it (blunt dissection) or be sharpened to present a sharp dissecting blade surface (sharp dissection).

The tip may also be constructed in a backwardly curved manner facing back towards the longitudinal axis of the cannula and with its reverse facing edge sharpened to facilitate resection or sharp dissection as it is retracted. This curved shape also serves to present a blunt profile that is less likely to perforate the anulus as it is advanced, even in the presence of uneven or degenerated anular tissue. Alternatively, the curved resection tip or blade may be formed as a multi-sided scoop with a concave trailing surface and convex leading surface such that it presents a blunt frontal profile even when advanced off-angle into the anulus or toward a vertebral endplate.

In another embodiment, the tip may be configured to house an ablation element. This element may be preferentially insulated on particular surfaces of the probe and/or tip to minimize unwanted damage to adjacent tissues. For example, the surface of the probe or tip facing an inner aspect of the anulus may be insulated to prevent unwanted travel through or harm other portions of the anulus, nucleus and vertebral endplates. Ablation energy is instead directed to the targeted tissue adjacent to the probe tip and not the endplates or tissue facing the insulted side of the probe tip.

FIG. 1A is an axial view along the transverse axis M of a vertebral body with the intervertebral disc 315 superior to the vertebral body. Axis M shows the anterior (A) and posterior (P) orientation of the functional spine unit within the anatomy. The intervertebral disc 315 contains the anulus fibrosus (AF) 310 which surrounds a central nucleus pulposus (NP) 320. Also shown in this figure are the left 370 and right 370' transverse spinous processes and the posterior spinous process 380.

Figure 1B:
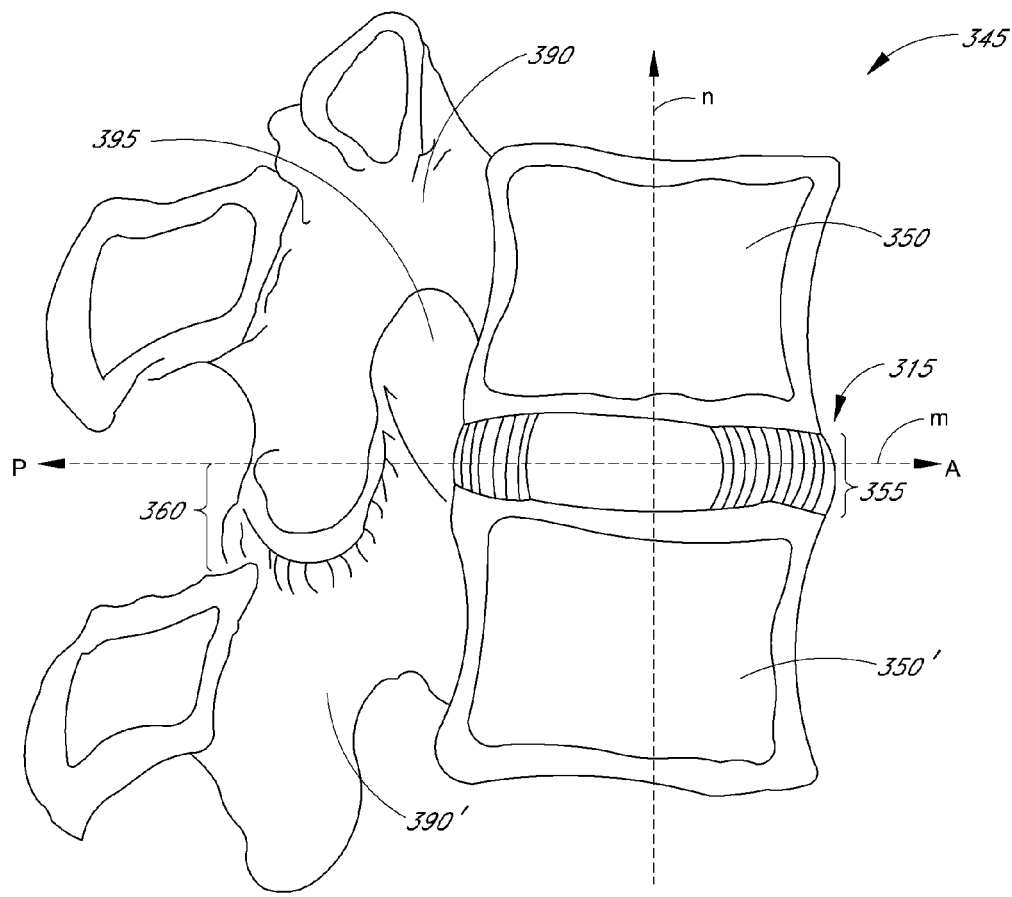
Figure 1C:
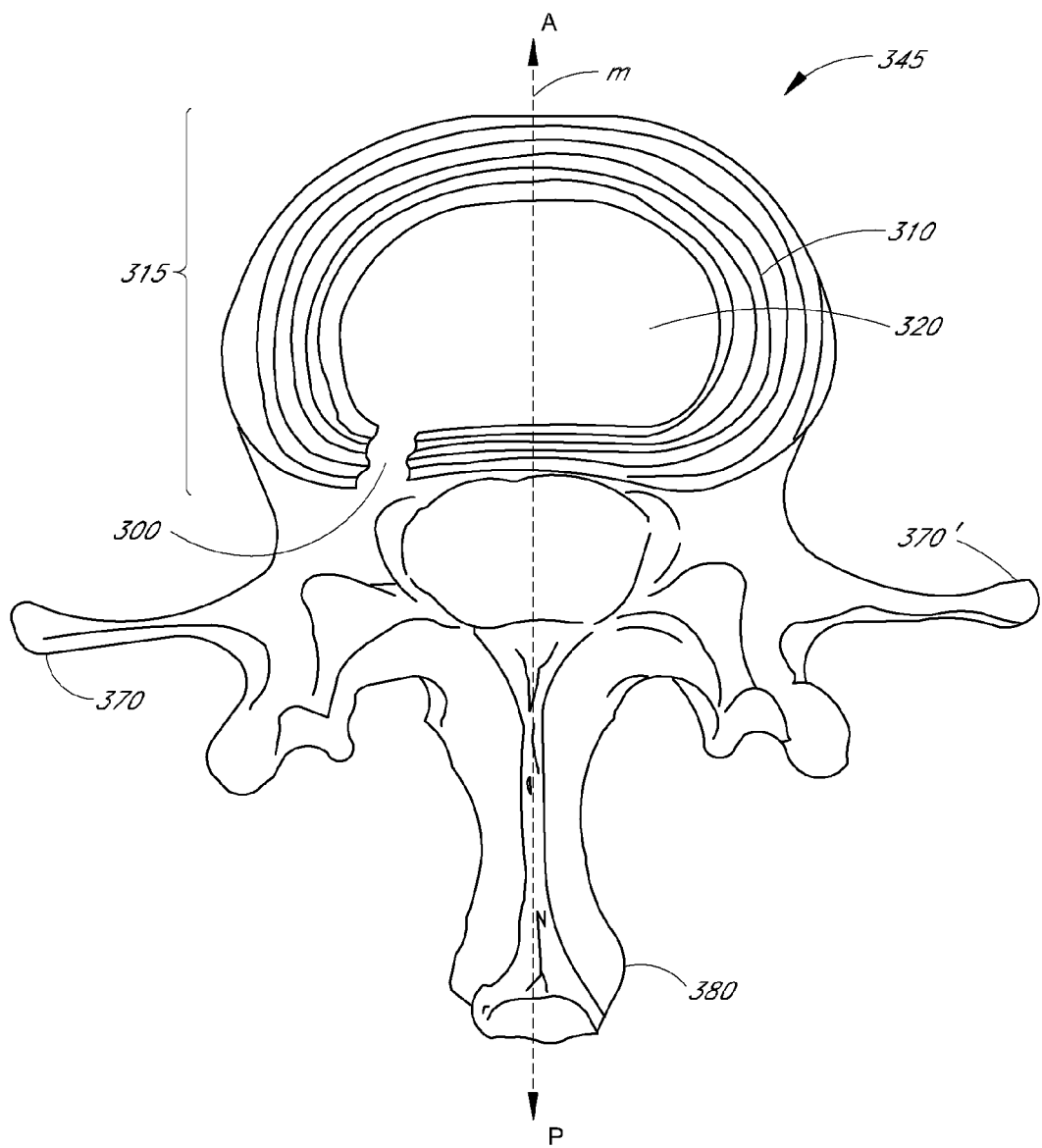
FIG. 1C shows the same functional spine unit with a defect in the anulus, which may have been created iatrogenically, as in the performance of an anulotomy, or may be naturally occurring.

FIG. 1B is a sagittal section along sagittal axis N through the midline of two adjacent vertebral bodies 350 (superior) and 350' (inferior). Intervertebral disc space 355 is formed between the two vertebral bodies and contains intervertebral disc 315, which supports and cushions the vertebral bodies and permits movement of the two vertebral bodies with respect to each other and other adjacent functional spine units.

Intervertebral disc 315 is comprised of the outer AF 310 which normally surrounds and constrains the NP 320 to be wholly within the borders of the intervertebral disc space. Axis M extends between the anterior (A) and posterior (P) of the functional spine unit. The vertebrae also include facet joints 360 and the superior 390 and inferior 390' pedicle that form the neural foramen 395.

Figure 2A:
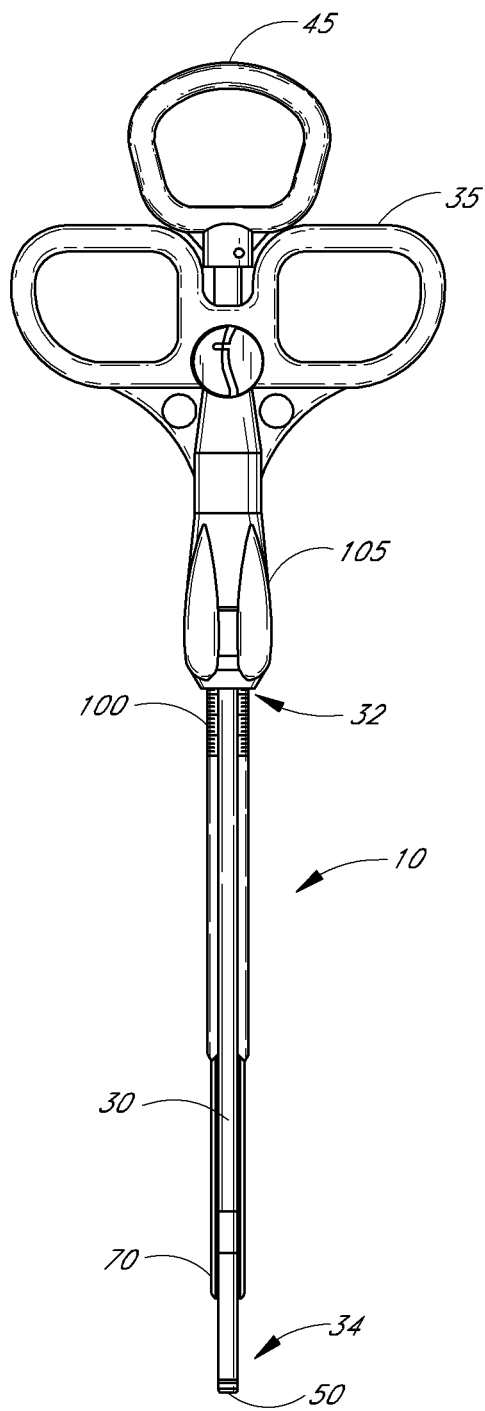
FIGS. 2A and 2B are front and side views of a device in accordance with the present invention.
Figure 2B:
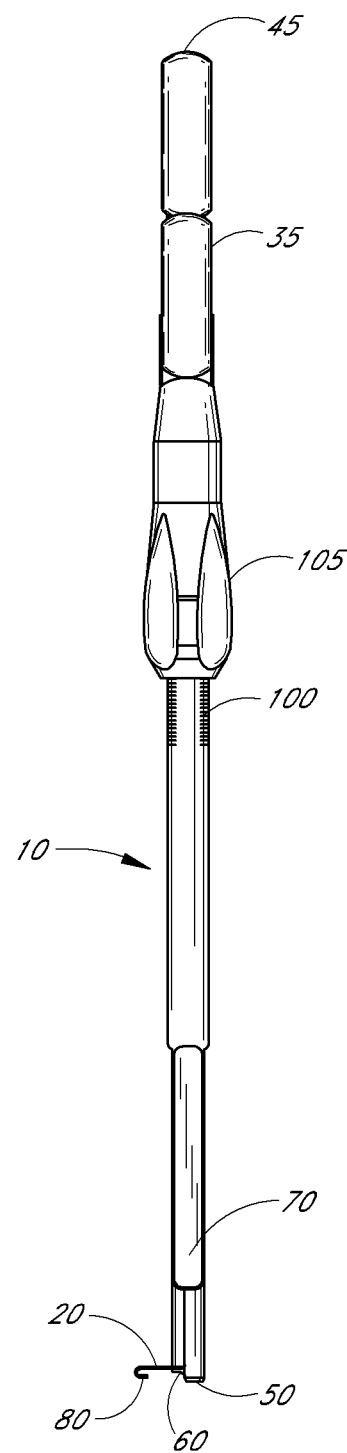
Figure 3:
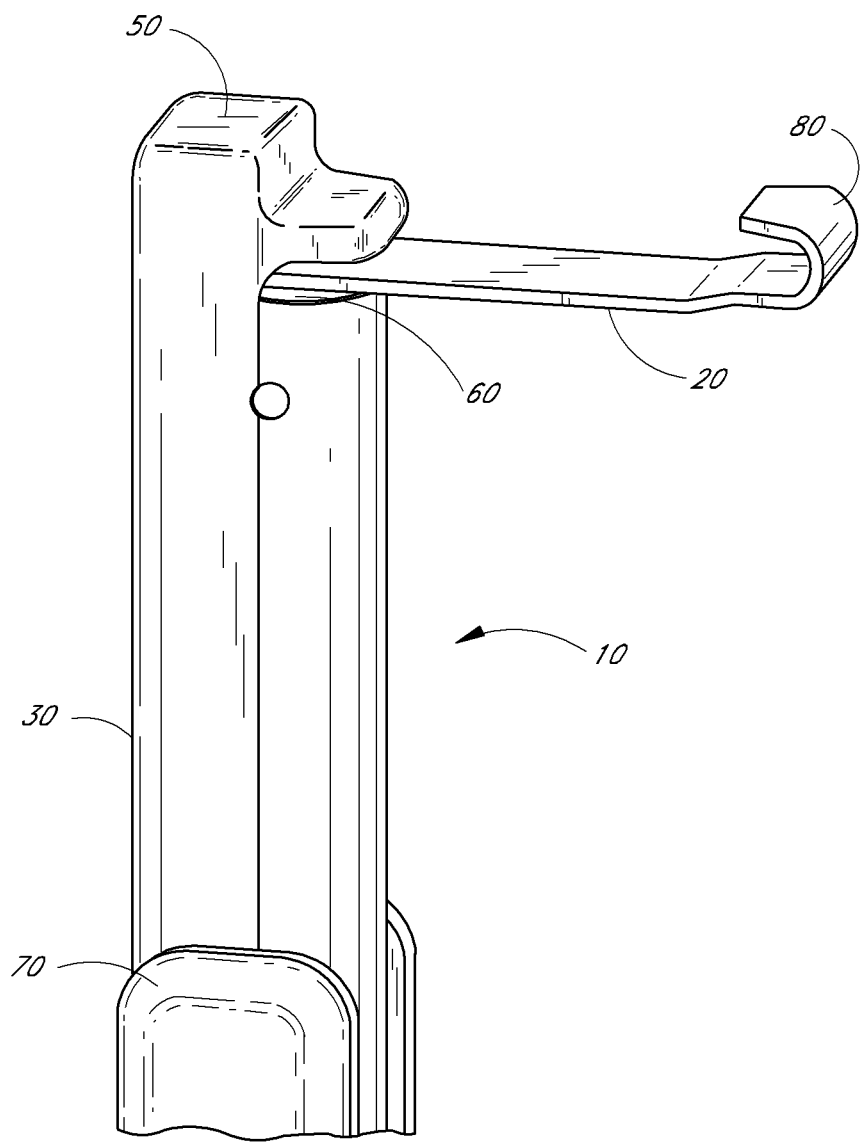
FIG. 3 is an isometric view of the distal end of the device.

Referring FIG. 2a, the device 10, a cannula handle 35, and a ring handle 45 are positioned such that the device 10 may be operated by one hand, i.e. utilizing the thumb, index, and ring fingers to position the device 10 and advance and retract the probe member 20. However, any of a variety of proximal handpieces can alternatively be used, including triggers, slider switches, rotatable knobs or other actuators to advance and retract the probe 20 as will be apparent to those of ordinary skill in the art in view of the disclosure herein.

In FIG. 5 the cannula handle 35 is secured to the proximal end 32 of an outer delivery cannula 30. Outer delivery cannula 30 extends from the proximal end 32 to a distal end 34 which is provided with an intradiscal tip 50. Delivery cannula 30 functions as a guide for the axial reciprocal movement of a push rod 40 as will be discussed. Delivery cannula 30 may, therefore, be provided in the form of an elongate tube having a central lumen for receiving push rod 40 therethrough. Alternatively, the guide may comprise a nontubular structure, in an embodiment in which the push rod travels concentrically over or alongside the guide.

The delivery cannula 30 may be manufactured in accordance with any of a variety of techniques well known in the medical device arts. In one embodiment, the cannula 30 comprises a metal tube such as stainless steel or other medical grade metal. Alternatively, the cannula 30 may comprise a polymeric extrusion such as high density polyethylene, PTFE, PEEK, PEBAX, or others well known in the medical device arts.

In general, the axial length of the delivery cannula 30 will be sufficient to reach the desired treatment site from a percutaneous or small incision access through the skin. Lengths within the range from about 10 centimeters to about 30 centimeters are contemplated, with a length from a proximal end 32 to distal end 34 within the range of from about 14 to about 20 centimeters contemplated for most posterior lateral access pathways. The length may be varied depending upon the intended access pathway and patient size.

Preferably, the outside diameter of the delivery cannula 30 is no greater than necessary to accomplish the intended functions disclosed herein. In general, outside diameters of less than one centimeter are preferred. In typical embodiments of the present invention, the delivery cannula 30 has an outside diameter of no greater than approximately 5 millimeters.

Referring to FIG. 6, the push rod or advancer 40 comprises an elongate body 42 having a proximal end 44 and a distal end 46. Push rod 40 may comprise a solid rod or tubular component as may be desired, depending upon the construction materials and desired physical integrity. In one embodiment, the push rod 40 comprises a solid metal rod, such as stainless steel or other suitable material. Alternatively, a polymeric extrusion using any of a variety of known medical grade polymers may be used.

Push rod 40 is preferably dimensioned to extend throughout the length of the delivery cannula 30, so that the probe 20 is fully extended from the intradiscal tip 50 when the ring handle 45 is brought into contact with the cannula handle 35 or other stop surface.

The device 10 may optionally be provided with one or more axially extending lumens, for placing the proximal end of the device 10 in fluid communication with the distal end, for any of a variety of purposes. For example, one or more lumens may extend through the push rod 40. Alternatively or in addition, the outside diameter of push rod 40 may be dimensioned smaller than the inside diameter of the delivery cannula 30 to create an annular space as is well understood in the catheter arts. A first lumen may be utilized for introduction of radiopaque dye to facilitate visualization of the progress of the probe 20 and or distal end of the device 10 during the procedure. The first lumen or second lumen may be utilized to introduce any of a variety of media such as saline solution, or carriers including any of a variety of medications such as anti-inflammatory agents e.g., steroids, growth factors e.g., TNFα antagonists, antibiotics, and functional proteins and enzymes e.g., chymopapain. A lumen may also be utilized to aspirate material such as nucleus pulposus, and/or to introduce nucleus augmentation material during or at the end of the procedure.

Figure 7:
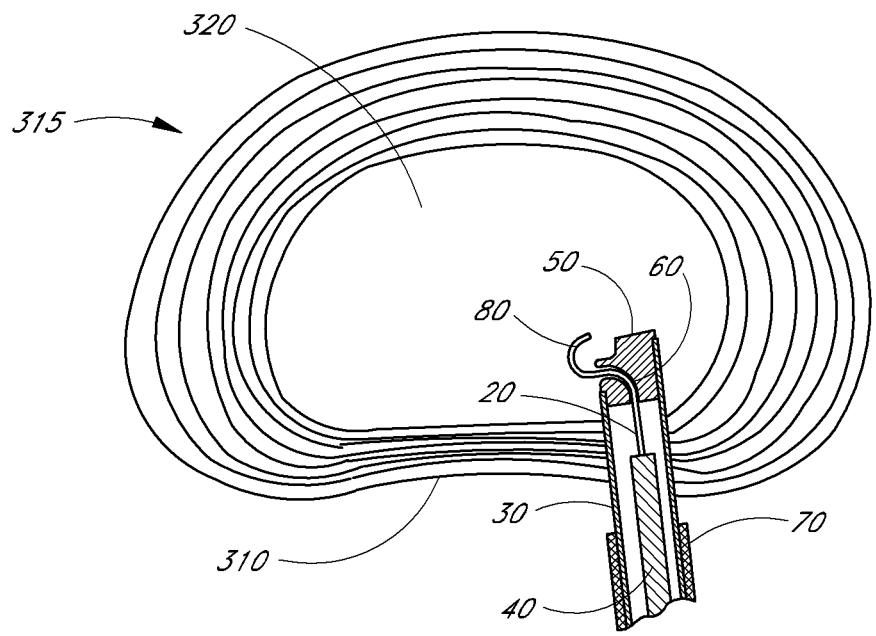
FIG. 7 is a cross-sectional view of the device with the intradiscal tip positioned within an anulotomy. The probe and depth stop are both retracted, and the distal end of the device has been inserted to a depth beyond the anterior aspect of the posterior anulus.

Referring to FIG. 7, the distal end 34 of device 10 is shown in cross section. Distal end 34 includes an axially moveable probe member 20, an outer delivery cannula 30 and an advancer or inner push rod 40. A curved passage or slot 60 is proximal an intradiscal tip 50 of the delivery cannula 30. The passage or slot 60 includes a curved distal deflection surface which acts to deflect the probe member 20 in a path that is roughly parallel to the lamellae of the posterior anulus fibrosus 310 as the probe member 20 is advanced outwardly from the curved slot 60 and into the disc 315 by the advancer 40.

The distal end 34 of the cannula 30 may be provided with any of a variety of constructions, depending upon the mode of deflection of the probe 20. In the illustrated embodiment, the distal end 34 is provided with a cap 52 which contains the deflection surface 62 therein. Cap 52 may be molded from any of the polymeric materials identified elsewhere herein, and secured to the distal end 34 by adhesive bonding, interference fit, or other conventional securing technique. Cap 52 has an atraumatic distal surface 50, which may comprise the distal end of cap 52, or may include a coating or layer of an atraumatic material such as silicone, carried by the cap 52.

Any of a variety of alternative deflection surfaces may be used, depending upon the desired distal tip design. For example, the distal molded cap 52 may be eliminated, and the deflection surface formed instead by an inside surface of the tubular cannula 30. This may be accomplished by providing two opposing axial slots extending proximally from the distal end 34 of the cannula 30 to isolate two opposing axial ribbons on the distal end 34. A first one of the ribbons is severed and removed, while the second one is curved across the central axis of the cannula 30 to provide a curved deflection surface.

Alternatively, the deflection surface may be eliminated in certain circumstances. For example, in the procedure illustrated in FIG. 7, the device is inserted through a defect in the posterior annulus at an angle relative to the desired treatment plane that requires the probe 20 to exit the device at a corresponding angle in order to advance the probe along the surface of or within the annulus as shown (e.g., within or parallel to the desired treatment plane). However, by moving the access path through the annulus roughly 80-90 degrees counterclockwise as viewed in FIG. 7, the longitudinal axis of the device 10 can be positioned coplanar or parallel to the posterior interior surface of the annulus or other desired treatment plane. In this orientation, the probe is desirably launched axially out of the end of the cannula 30, to dissect a space for subsequent annulus patch implantation.

The foregoing axial launch embodiment of the invention may be utilized through the naturally occurring defect. However, the axial launch device is more likely to find application through an iatrogenic access pathway, created through the annulus spaced apart from the natural defect such that the longitudinal axis of the iatrogenic access is substantially parallel (e.g., no more than about +/−20 degrees) from the plane in which the natural defect resides.

As a further alternative, the probe 20 may be laterally deflectable in response to manipulation of a deflection control at the proximal end of the device 10. For example, the probe 20 in one construction comprises a flexible metal or polymeric ribbon, extending from the distal end of the advancer 40 or other axial support. An axially extending steering element is attached to the probe 20. Generally the steering element will be attached near the distal end of the probe 20. Axial proximal or distal movement of the steering element relative to the advancer 40 will cause a lateral deflection of the probe 20.

The radius of curvature of the deflection can be controlled in a variety of ways as will be apparent to those of skill in the art in view of the disclosure herein, such as by varying the lateral flexibility of the probe 20, and the attachment point of the steering element to the probe 20. Due to the differing physical requirements of devices under tension compared to compression, the cross section of the device may be minimized if the steering element is a pull wire or ribbon such that axial proximal retraction of the pull wire relative to the probe 20 causes a lateral deflection of the probe 20. The lateral deflection can be coordinated with the extent of distal advance to cause the probe to follow the desired curved path either by mechanics in the proximal handpiece, or by the clinician. For this purpose, the proximal handpiece can be provided with any of a variety of controls, such as slider switches or rotatable levers or knobs to allow the clinician to control deflection as well as distal (and lateral) advance.

In an alternate construction, the probe launches axially from the distal end 34 of the cannula or other guide 30, but curves under its own bias to travel in a lateral arc and slide along the posterior annulus or other desired surface. This may be accomplished by constructing the probe from a nickel-titanium alloy such as Nitinol and providing it with a lateral pre bent orientation. The probe is restrained into an axial orientation within the cannula 30, but extends laterally under its own bias as it is advanced distally from an opening in the distal end of the cannula 30.

The probe member 20 in the illustrated embodiment may be formed from a superelastic nickel titanium alloy, or any other material with suitable rigidity and strain characteristics to allow sufficient deflection by deflection surface 62 without significant plastic deformation. The probe member 20 can be formed from an elongated sheet, tube, rod, wire or the like. Probe 20 may also be constructed in various cross-sectional geometry's, including, but not limited to hemicircular, semicircular, hollow, and rectangular shapes.

A probe tip 80 at the distal end of the probe member 20 can be used to dissect between the anulus 310 and nucleus 320, to dissect between layers of the anulus 310, or to dissect through the nucleus. The probe tip 80 can be constructed of the same material as the probe member 20 or another suitable material for the purposes of cutting or presenting a blunt rounded surface. A sharpened surface on the distal edge of the probe member 20 forming the probe tip 80 can be used to dissect a path to enable the insertion of an implant in the created space. Similarly, a blunted tip profile may be used to separate or disrupt anular lamella and create an open space between the anulus 310 and nucleus 320 or within the nucleus 320 itself.

The probe tip 80 may also be provided with a backward curve as shown in FIGS. 11A and 11B. In this construction, a concave surface faces the longitudinal axis of the device when deployed within the disc. The tip 82 may be sharpened to facilitate resection or sharp dissection as it is retracted. This curved shape will also serve to present a blunt profile to reduce the risk of perforating the anulus 310 as it is advanced, even in the presence of uneven or degenerated anular tissue. The curved tip 80 may be formed in any of a variety of radii or shapes depending on the amount of material one desires to remove on each pass of the probe member 20 into the disc, as shown in FIGS. 13A and 13B. Alternatively, the resection tip 80 or blade may be formed as a multi sided concave scoop 81 having a cavity therein such that it presents a blunt convex frontal profile even when advanced off-angle into the anulus 310 or toward a vertebral endplate 350, as shown in FIGS. 15A and 15B. Also, the increased surface area of such a scoop 81 would serve to further facilitate removal of disc tissue.

The distal end of device 10 is shown in FIG. 7 as inserted through a defect in the posterior anulus 300. Alternatively, the device 10 could be inserted through defects in the posterior-lateral, lateral, or anterior anulus 300. In these alternate positions, the probe tip 80 can be advanced parallel to the lamellae of different regions of the anulus 310. One of the many advantages of the curved, distal probe tip 80, as represented in several embodiments of the current invention, is its minimal profile when the probe is in its retracted state relative to the outer cannula 30. In this state, depicted in FIG. 7, the curved tip 80 fits around the distal end of intradiscal tip 50, only minimally increasing the size or profile of device 10. This minimizes the size of the defect in the anulus 300 necessary to allow proper insertion of the distal end of device 10.

As demonstrated in FIGS. 11 and 13, various geometry's of the tip 80 can be employed without increasing the necessary anular defect or anulotomy 300 size for insertion of the intradiscal tip 50 of the device 10. For example, the larger radius of the probe tip 80 in FIG. 13 presents a blunter dissection profile when advanced from the intradiscal tip 50 without necessitating a correspondingly larger anulotomy 300 for proper insertion of the device 10 into the disc. As the bluntness of probe tip 80 is increased, it may be desirable to increase the stiffness of the probe 20. This increased stiffness may be achieved in a variety of ways which can include, but is not limited to using a thicker or more rigid material for forming probe 20, or by using a curved cross-sectional shape along the length of probe 20. These techniques may be used to stiffen all or a portion of the length of probe 20.

Figure 17A:
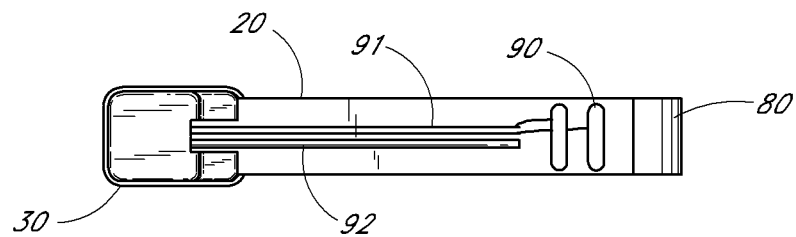
FIG. 17A is a top view.
Figure 17B:
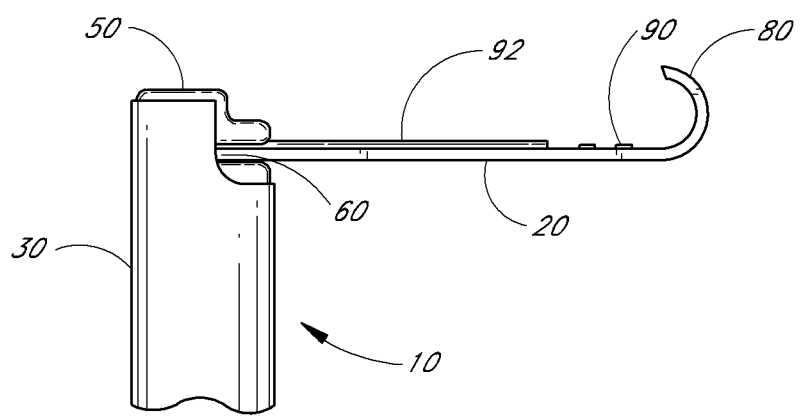
FIG. 17B is a side view of the distal end of the device of an embodiment of the invention. The probe includes an ablation unit, control wires, and a tube, mounted to the probe proximal of the distal tip. The anvil of the device has material removed in its central area to allow the retraction of the tube and control wires into the device.

The probe tip 80 may also be coupled to an ablation unit for ablating tissue, as shown in FIGS. 17A and 17B. The ablation unit can be attached to the probe member 20 preferably on the side facing the interior of the disc and proximal to the probe tip 80. In this configuration, the probe member 20 acts as a mechanical and thermal barrier minimizing unwanted ablation in the direction opposite the ablation unit, i.e. in the direction facing the interior aspect of the anulus. Ablation may be achieved using any of a variety of energy delivery techniques including, but not limited to light (laser), radio-frequency or electro-magnetic radiation in either unipolar or bipolar configurations, resistive heating of the probe, ultrasound or the like.

An embodiment of a bipolar radio-frequency unit is depicted in FIG. 17. Power and control wires 91 may be deposited directly on to the probe member 20 as is known in the art. These wires act to connect RF elements 90 to an external power source and control unit affixed to or in communication with the advancer 40 and cannula 30. These elements 90 serve to allow the conduction of current therebetween, resulting in a resistive heating of the tissue in the region of the probe tip 80. These elements 90 are shown proximal to the distal probe tip 80 of device 10, but may be positioned at any location along probe 20 and/or on probe tip 80. Only two elements 90 are shown, however numerous elements may be positioned at various locations along the entire length of the probe 20 and be activated individually or multiplexed in pairs or groups to produce a desired temperature profile or ablation within the disc tissue.

Tube 92 is shown attached to probe 20 to provide an escape path for vapor and material ablated or for the infusion of fluids or gasses. These fluids or gasses may be added to alter the conductive characteristics of the tissue or may include various drugs, medications, genes or gene vectors or other materials to produce a desirable therapeutic effect. Tube 92 is shown with a single distal orifice. It may alternatively comprise any number of side holes or channels to increase the spread of fluids or gasses within the tissue or similarly to remove such materials as required by the procedure. Axial lumen are provided as needed to place the side holes or other apertures in communication with the proximal end of the device 10. The ablation unit could be activated as the probe member 20 is advanced through the tissues to create a cavity or activated as the probe member 20 is retracted after it has been advanced to a desired distance. Moreover, the power supplied to the ablation unit 90 could be varied according to the instantaneous velocity of the probe member 20 in order to ablate a more uniform cavity within the disc.

Whether used to dissect, resect or ablate tissue within the disc, device 10 may be used as part of an implantation procedure by creating a cavity or dissected region into which any of a variety of intradiscal implants or medications may be inserted. This region may be between or within anular layers 310, within the nucleus 320, or between the anulus 310 and nucleus 320 or within a defect. It may include a portion or the entirety of the nucleus. Increasing amounts of disc tissue may be removed by advancing and retracting the probe tip repeatedly at different depths within the disc. Intradiscal implants may be inserted independently using separate instrumentation or along, through, or around probe 20. Suitable implants include, among others, those disclosed in U.S. patent application Ser. No. 09/642,450 filed Aug. 18, 200, now issued as U.S. Pat. No. 6,482,235, entitled Devices and Methods of Vertebral Disc Augmentation, the disclosure of which is incorporated in its entirety herein by reference. As disclosed in U.S. Pat. No. 6,482,235, suitable implants include one or more anchors and/or support members, such as sutures, bone anchors, soft tissue anchors, tissue adhesives, and materials that support tissue ingrowth. These may be permanent devices or resorbable. Any attachment to a portion of the functional spine unit and a herniated segment must be strong enough to resist the tensional forces that result from repair of a hernia and the loads generated during daily activities. The implant may also comprise a barrier. In one embodiment, the barrier is inserted into the interior of the disc and positioned proximate to the interior aspect of an anulus defect. The barrier material is preferably considerably larger in area than the size of the defect, such that at least some portion of the barrier means abuts healthier anulus fibrosis. The device acts to seal the anulus defect, recreating the closed isobaric environment of a healthy disc nucleus. This closure can be achieved simply by an oversizing of the implant relative to the defect. It can also be achieved by affixing the barrier means to tissues within the functional spinal unit. In a preferred aspect of the present invention, the barrier is affixed to the anulus surrounding the anulus defect. This can be achieved with sutures, staples, glues or other suitable fixation means or fixation device. The barrier means can also be larger in area than the defect and be affixed to a tissue or structure opposite the defect, i.e. anterior tissue in the case of a posterior defect. The barrier means is preferably flexible in nature. It can be constructed of a woven material such as Dacron or Nylon, a synthetic polyamide or polyester, a polyethplene, and can further be an expanded material, such as expanded polytetrafluroethelene (e-PTFE), for example. The barrier means can also be a biologic material such as cross-linked collagen or cellulous. The barrier means can be a single piece of material. It can have an expandable means or component that allows it to be expanded from a compressed state after insertion into the interior of the disc. This expandable means can be active, such as a balloon, or passive, such as a hydrophilic material. The expandable means can also be a self-expanding elastically deforming material, for example. The barrier can be mounted within an anulus and covering an anulus defect. The barrier can be secured to the anulus with a fixation mechanism or fixation means. The fixation means can include a plurality of suture loops placed through the barrier and the anulus. Such fixation can prevent motion or slipping of the barrier away from the anulus defect. The barrier means can also be anchored to the disc in multiple locations. In one preferred embodiment, the barrier means can be affixed to the anulus tissue in or surrounding the defect and further affixed to a secondary fixation site opposite the defect, e.g. the anterior anulus in a posterior herniation, or the inferior or superior vertebral body. For example, fixation means can be used to attach the barrier to the anulus near the defect, while an anchoring mechanism can secure the barrier to a secondary fixation site. A connector can attach the barrier to the anchor. Tension can be applied between the primary and secondary fixation sites through a connector so as to move the anulus defect toward the secondary fixation site. This may be particularly beneficial in closing defects that result in posterior herniations. By using this technique, the herniation can be moved and supported away from any posterior neural structures while further closing any defect in the anulus. The barrier means can further be integral to a fixation means such that the barrier means affixes itself to tissues within the functional spinal unit.

Figure 22A:
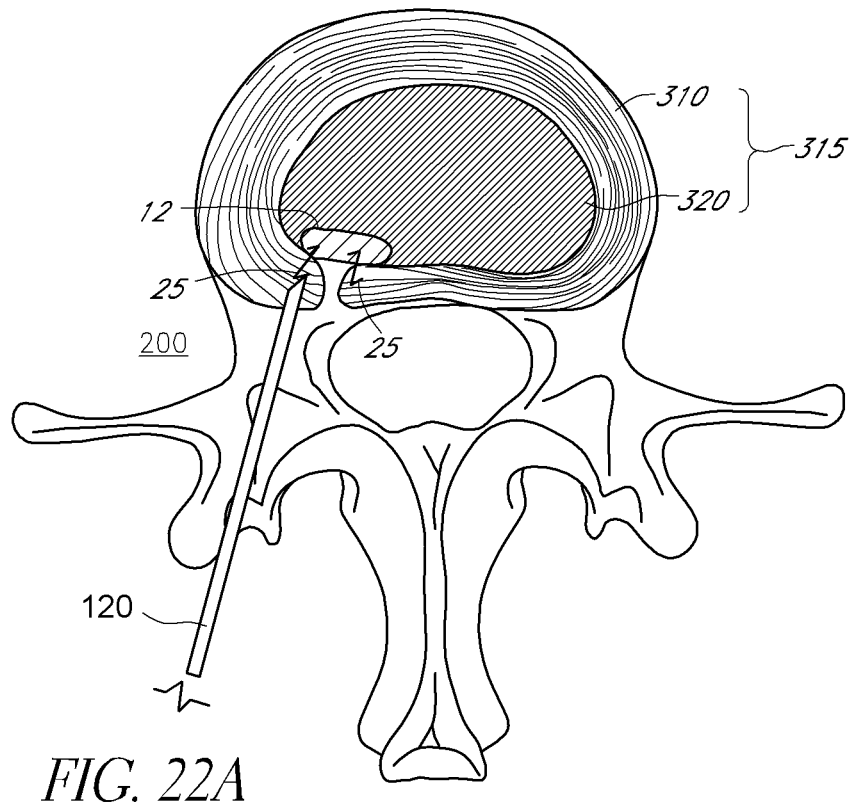
FIG. 22A depicts an embodiment of the barrier means of the present invention being secured to an anulus using fixation means.
Figure 22B:
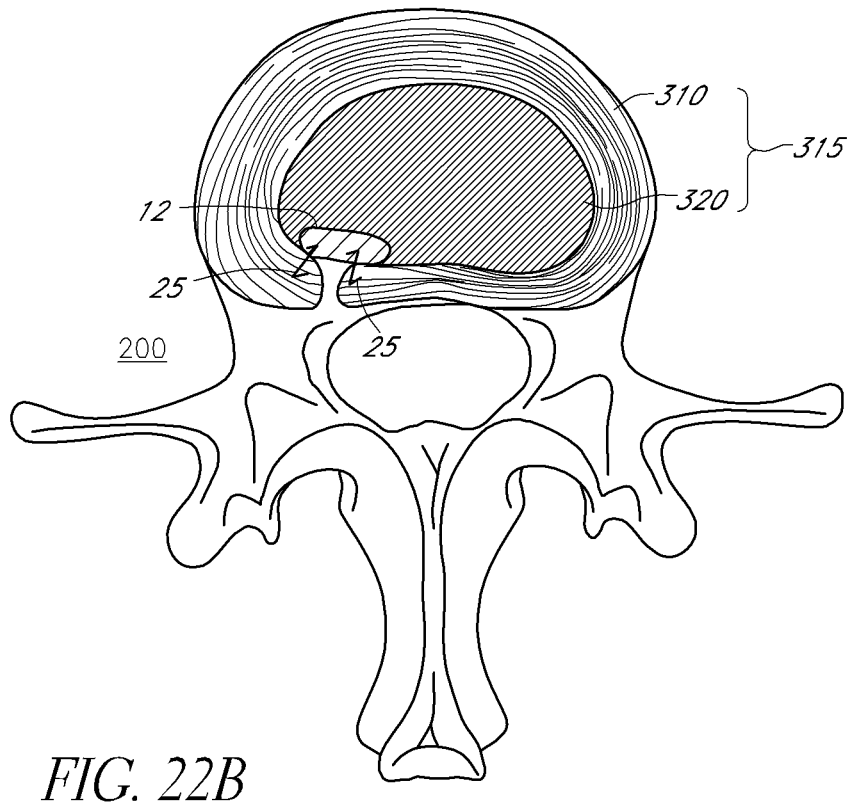
FIG. 22B depicts an embodiment of the barrier means of FIG. 22A secured to an anulus by two fixation darts wherein the fixation tool has been removed.

Another method of securing the barrier means 12 is to insert the barrier means 12 through the defect or another opening into the disc 315, position it proximate to the interior aspect of the defect, and pass at least one fixation means 25 through the anulus 310 and into the barrier 12. In a preferred embodiment of this method, the fixation means 25 can be darts and are first passed partially into anulus 310 within a fixation device 120, such as a hollow needle. As depicted in FIGS. 22A and 22B, fixation means 25 can be advanced into the barrier means 12 and fixation device 120 removed. Fixation means 25 preferably have two ends, each with a means to prevent movement of that end of the fixation device. Using this method, the fixation means can be lodged in both the barrier 12 and anulus fibrosus 310 without any aspect of fixation means 25 exterior to the disc in the extradiscal region 200. Fixation means (or anchor) 25 can be securely established within a portion of the functional spine unit in the usual and customary manner for such devices and locations, such as being screwed into bone, sutured into tissue or bone, or affixed to tissue or bone using an adhesive method, such as cement, or other suitable surgical adhesives. Once established within the bone or tissue, fixation means (or anchor) 25 should remain relatively stationary within the bone or tissue.

Figure 23A:
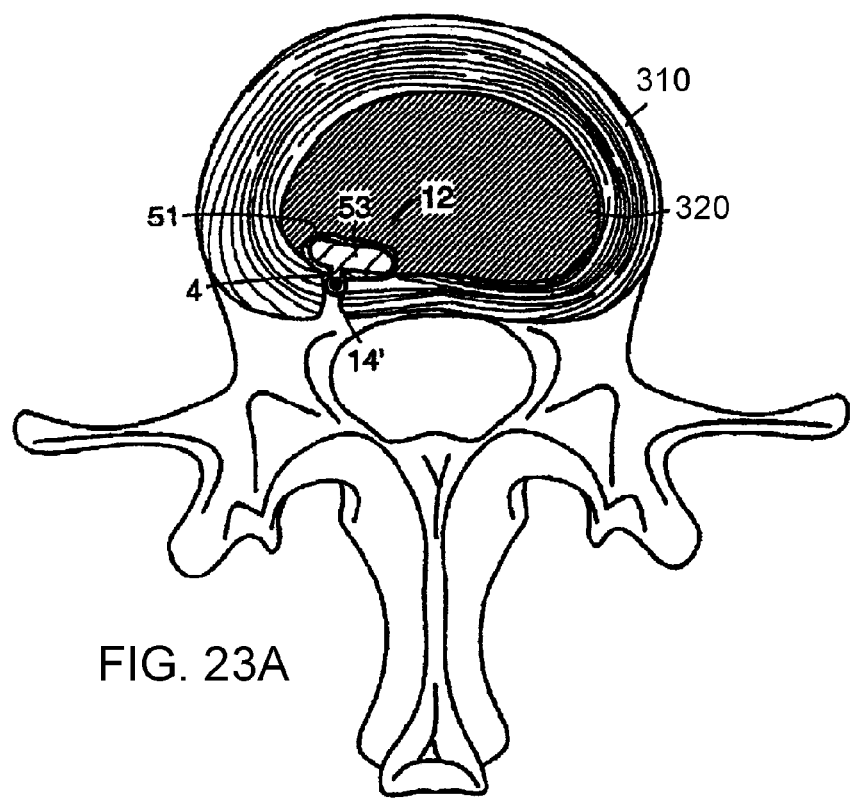
FIG. 23A shows an alternative fixation scheme for the sealing means and enlarging means.
Figure 23B:
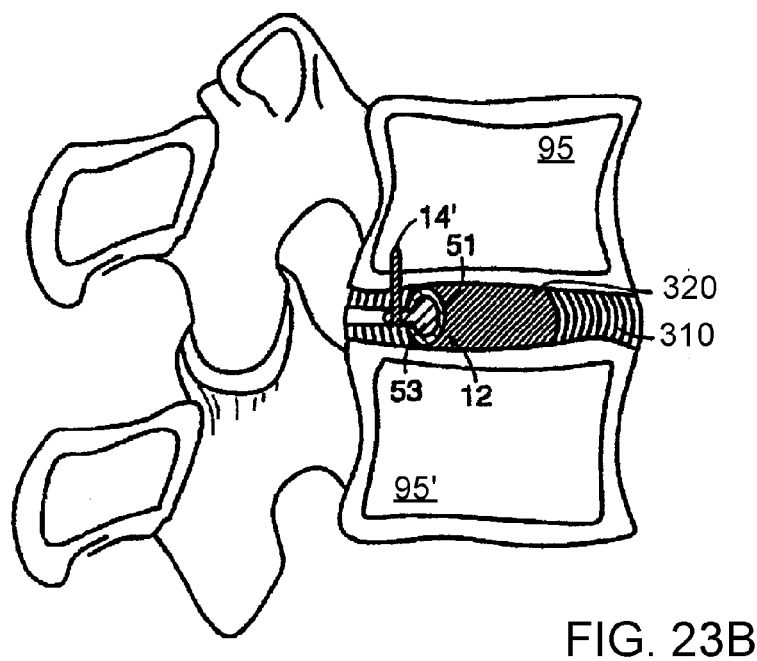
FIG. 23B shows the construct of FIG. 23A in a sagittal section with an anchor securing a fixation region of the enlarging means to a superior vertebral body in a location proximate to the defect.

As discussed above, an implant such as a barrier can be anchored or attached to a vertebral body or other tissues of a functional spinal unit. Another method of securing the barrier 12 to tissues is to affix an enlarging means 53 to tissues either surrounding or remote from the defect 16. The enlarging means 53 can have an integral fixation region 4 that facilitates securing it to tissues as depicted in FIGS. 23A and 23B. This fixation region 4 can extend exterior to sealing means 51 either through opening 38 or through a separate opening. Fixation region 4 can have a hole through which a fixation means or fixation device 14 can be passed. In a preferred embodiment, the barrier 12 is affixed to at least one of the surrounding vertebral bodies (95 and 95') proximate to the defect using a bone anchor 14'. The bone anchor 14' can be deployed into the vertebral bodies 95, 95' at some angle between 0° and 180° relative to a bone anchor deployment tool. As shown the bone anchor 14' is mounted at 90° relative to the bone anchor deployment tool. Alternatively, the enlarging means 53 itself can have an integral fixation device 14 located at a site or sites along its length.

Figure 8:
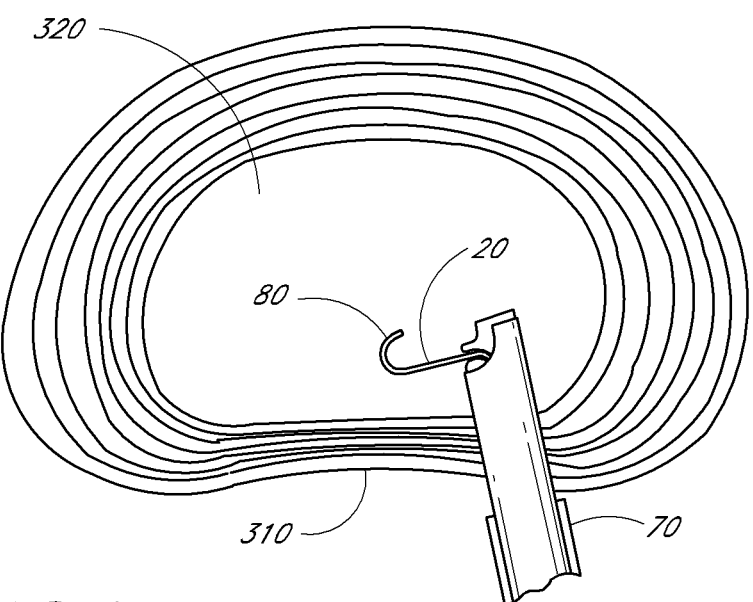
FIG. 8 depicts the probe of the device advanced relative to its starting position in FIG. 7 above.

FIGS. 7, 8, 9, and 10 depict an embodiment of the device 10 placed within an anulotomy or defect of anulus 300, which can be used to measure the thickness of anulus 310. In FIG. 7, the distal portion of the cannula 30 defined by the intradiscal tip 50 is inserted through the anulotomy or defect 300 to a depth wherein the probe 20 is inserted just beyond the anterior border of the posterior anulus 310. In FIG. 8, the probe member 20 is advanced out of cannula 30 and deflected by the deflection surface in curved passage 60 of the intradiscal tip 50 at an angle nearly perpendicular to device 10, causing the probe member 20 to advance parallel to the inner surface of the posterior anulus 310. In this use, the probe 20 need only be advanced outward several millimeters.

Figure 9:
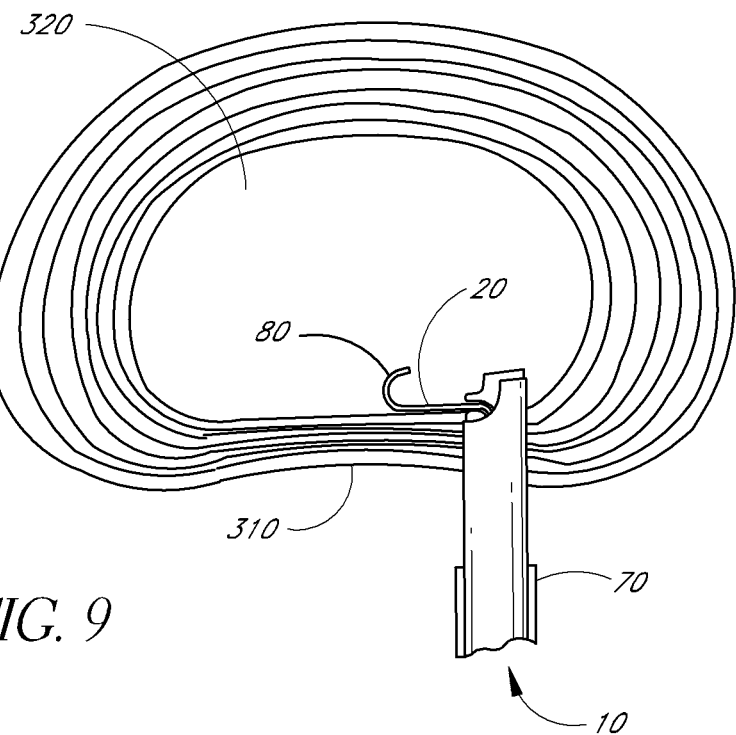
FIG. 9 depicts the intradiscal tip of the device with the probe resting on the inner surface of the posterior anulus.
Figure 10:
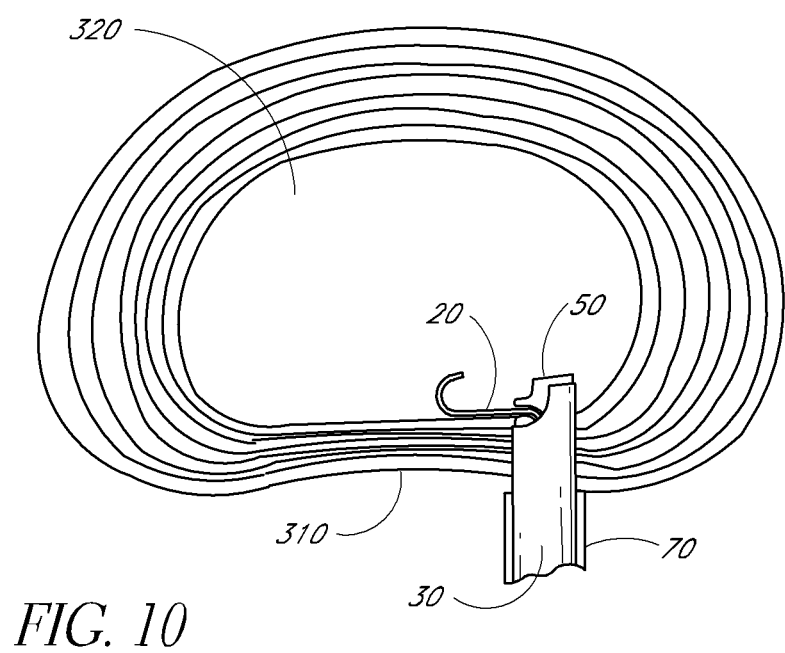
FIG. 10 depicts the device with the depth stop advanced to the posterior surface of the posterior anulus.

In FIG. 9, device 10 is proximally retracted from the anulotomy 300 until the probe 20 contacts the posterior anulus 310. In FIG. 10, a slideably adjustable depth stop 70 is carried by the cannula 30 and advanced distally (anteriorly) until it contacts the exterior surface of the posterior anulus 310 and the probe member 20 is in contact with the interior surface of the posterior anulus 310. The depth stop 70 functions by abutting anular tissue or surfaces of the vertebral body adjacent to the anulotomy 300 which impede further entry of the cannula 30 into the disc, such as may be determined by tactile feedback or under fluoroscopic visualization. FIG. 4 shows the depth stop adjustment knob 105, calibrated measurement marks 100 and depth stop 70. The cannula 30 or depth stop 70 may be marked with calibrated measurements 100 so that the distance between the intradiscal tip 50 at the point where the probe member 20 exits and the depth stop 70, can be determined. This distance corresponds to the thickness of the anulus adjacent to the anulotomy 300.

Figure 18:
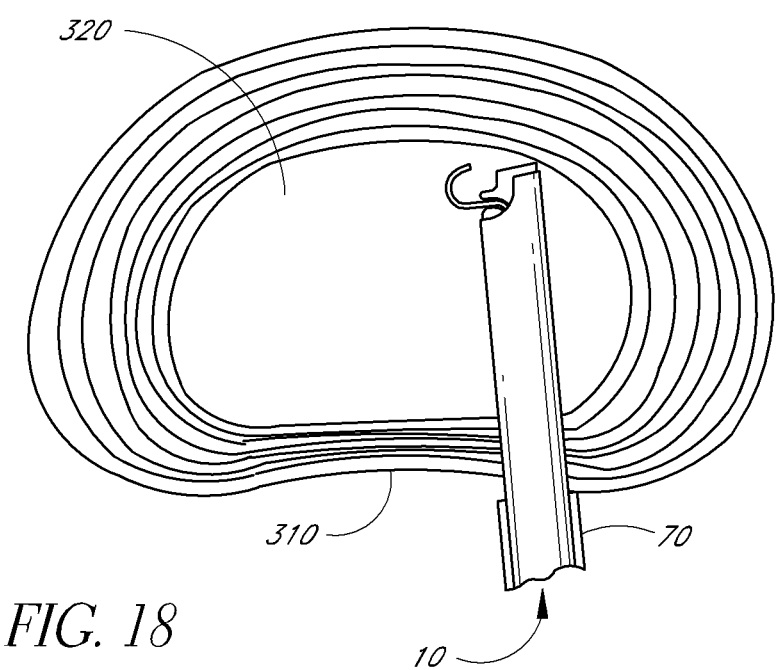
FIG. 18 is a transverse view of the intervertebral disc wherein the device is being used to measure the anterior to posterior distance from the anulotomy to the inner aspect of the anterior anulus.

FIG. 18 depicts an embodiment of the device 10 placed within an anulotomy or defect in anulus 300 and being used to determine the anterior-posterior dimension of the nuclear space as defined by the distance between the inner surfaces of the posterior anulus and the anterior anulus. Here, the probe member 20 and the adjustable depth stop 70 are fully retracted. The probe 20 and advancer 40 may be eliminated entirely in an embodiment intended solely for the anterior-posterior measurement described herein. The intradiscal tip 50 of the device 10 is advanced through the anulotomy or defect in anulus 300 until the inner surface of the anterior anulus is reached and impedes further travel of the intradiscal tip 50. In this manner the device 10 is used to provide tactile feedback of the disc's internal geometry. The adjustable depth stop 70 is then advanced distally toward the proximal exterior surface of the anulus or vertebral body and reading of the maximum depth reached can be obtained via calibrations on the proximal end of the device such as on the cannula. Electronic or other means could also be employed to measure and display this distance. The posterior anular thickness value can be subtracted from this to yield the distance between the inner aspects of the posterior and anterior anulus.

Figure 19:
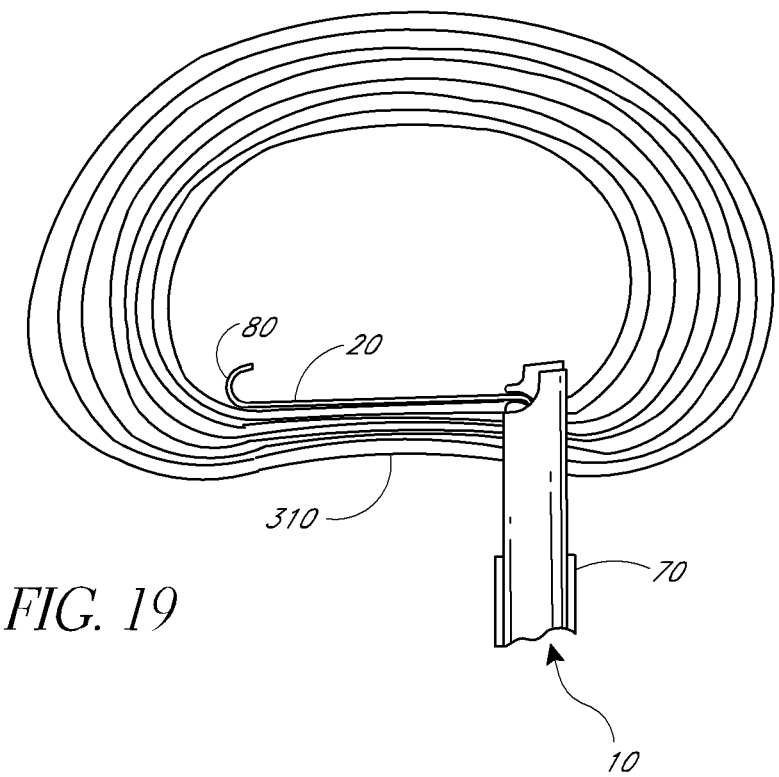
FIG. 19 is a transverse view of the intervertebral disc wherein the probe is advanced from the anulotomy to the far lateral corner.
Figure 20:
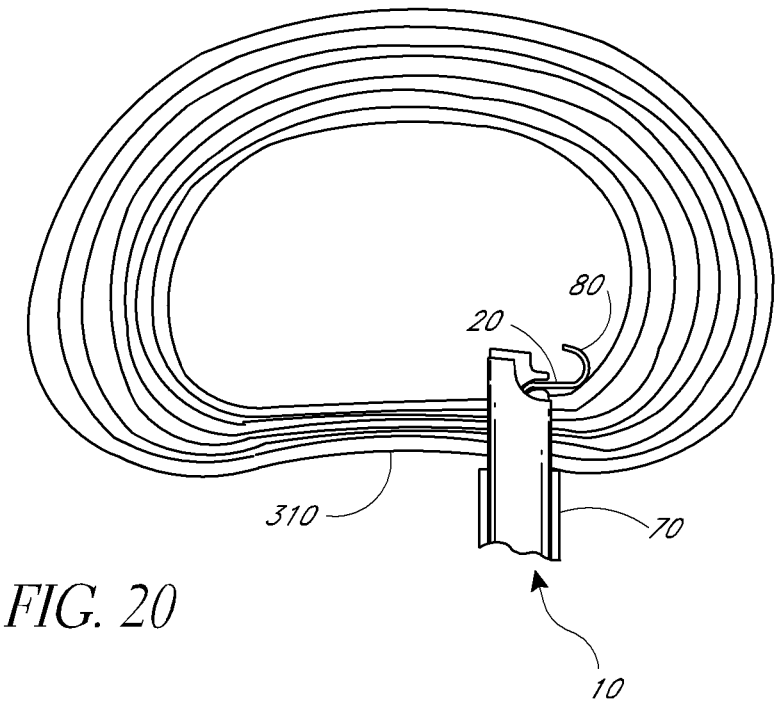
FIG. 20 is a transverse view of the intervertebral disc wherein the probe is advanced from the anulotomy to the near lateral corner.

FIGS. 19 and 20 depict an embodiment of the device 10 placed within an anulotomy or defect in anulus 300 and being used to determine the distance between the left and right lateral interior surfaces of the anulus. In measuring the distance between the left and right lateral surfaces of the anulus 310 the intradiscal tip 50 is inserted just beyond the interior wall of the posterior anulus, the probe tip 80 is advanced out of the curved passage 60 in the plane of the disc, i.e. parallel to the endplates, until tactile feedback from the advancer 40, indicates that lateral surface is resisting further advancement. Calibrated makings on the advancer 40 visible through or proximal to the cannula can then be used to determine this distance.

By rotating the device 10, while the probe member 20 is fully retracted, 180 degrees and performing the same action in the lateral direction, as shown in FIG. 20, one can obtain the total distance between the interior lateral surfaces. This method may be repeated at various depths within the disc by adjusting the depth stop 70. A similar method of using the probe member 20 to tactically interrogate the interior of the disc may be employed to dimension the distance between the vertebral endplates and relative distances from the anulotomy 300 to the endplates. All of the foregoing measurements may be taken either using a scoop shaped distal tip as shown, or a blunt, atraumatic tip without a scoop to minimize disruption of the nucleus.

The measurement techniques described above may also be used to achieve the complete resection of the nucleus from the disc space. For example, a resection or ablation tip as described above may be passed repeatedly into the disc to the lateral borders of the nucleus. This process may be repeated at varying depths within the disc from the inner aspect of the posterior anulus to the inner aspect of the anterior anulus as determined by the depth stop.

Figure 21A:
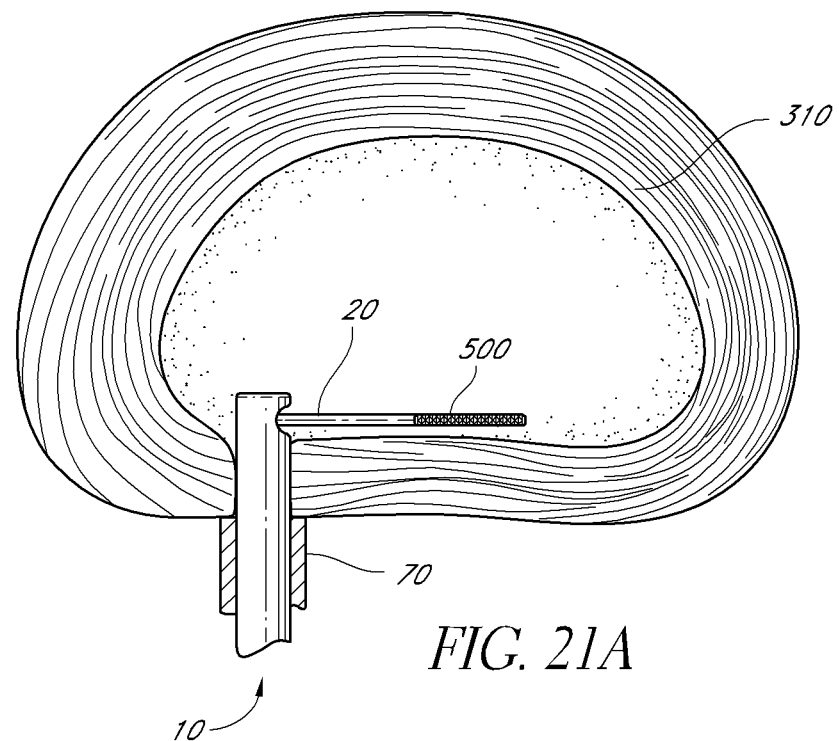
FIGS. 21A and 21B are transverse views of the intervertebral disc.
Figure 21B:
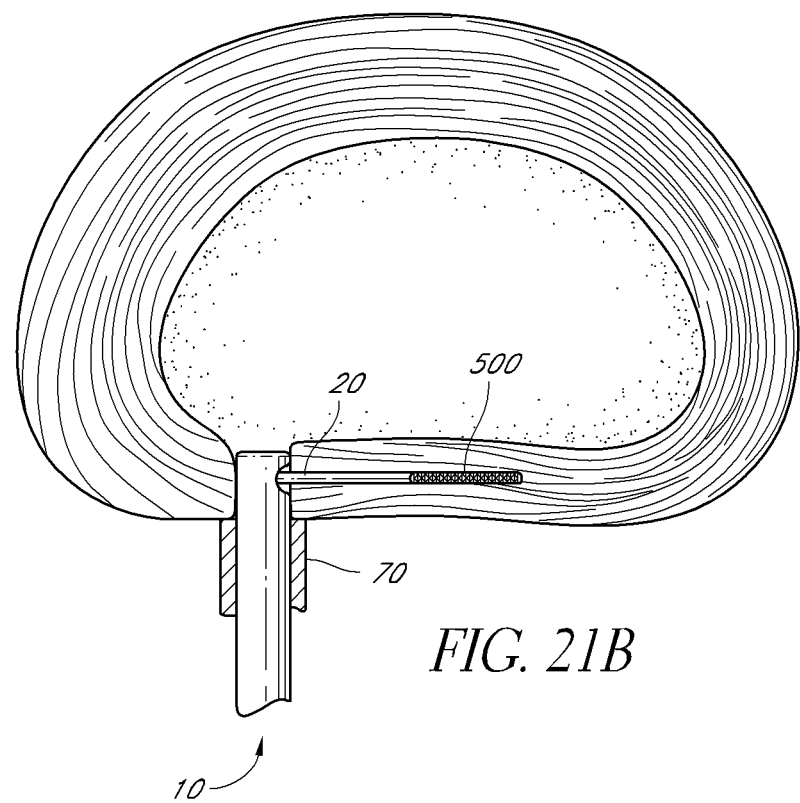

Through adjustments to the depth stop 70 setting, the device 10 may be used in various procedures at different locations within the disc such as dissection or resection of a space within the disc and also placement of another intradiscal instrument or implant. More generally, the depth stop may be used as part of a method of performing a procedure within the disc at a certain location. For example, as shown in FIG. 21A, this method may be particularly useful for placing an implant 500 along an inner surface of the anulus fibrosus. The depth stop 70 or soft/bony tissue alignment means can engage or simply rest against the anulus or a portion of one or more vertebral bodies and can serve to align and stabilize the device for consistent deployment of a probe, intradiscal implant or agent. The alignment means can be concentric to the cannula or offset, and can be embodied as one or more projections or "feet" extending outward from cannula. The thickness of the anulus as determined by any of the measurement techniques described above may be used for setting depth stops alignment means on other implantation instruments used to place an implant along an anulus lamella. As an example, if the posterior anulus is measured to be 7 mm thick using device 10, a depth stop may be set on an implantation instrument to limit the penetration of this instrument into the disc to 7 mm or another depth that is relative to 7 mm. This would allow for an implant placed by this instrument to be inserted into a space previously dissected within the disc by device 10 along the inner lamellar surface of the posterior anulus. Setting the depth stop 70 for a value less than, for example 7 mm (in this example), would allow for deployment of an implant 500 between lamella as depicted in FIG. 21B. Alternatively, setting the depth stop 70 for a value greater than, for example 7 mm (in this example), would provide for implantation within the nucleus.

As discussed above, it may be desirable for medical professionals to determine the location of the interface between the nucleus and anulus for selecting an implant site or for delivering therapeutic or diagnostic agents. This can be achieved through tactile feedback from the various embodiments of the devices described herein, imaging equipment, or via transducers coupled to the devices. Biophysical or biochemical transducers could be designed to differentiate or indicate the disparate properties between anulus tissue and nucleus pulposus tissue. Such transducers could, for example, be used to indicate the difference in pH, tissue density, hydration, reflectance, light absorption, thermal transmission or any of a number of tissue surveillance techniques known to those skilled in the art.

Probe 20 may be used as part of the placement of an intradiscal implant in any of a variety of ways. One advantageous use of the probe 20 can be achieved by detaching it from advancer 40 once probe 20 is in a desired position within the disc space. Implants including those depicted in FIGS. 21A and 21B may then be passed along, behind or in front of probe 20 into this desired position. An implant can also be coupled to the probe 20 and then detached upon delivery. Probe 20 may then be removed from the disc space.

While this invention has been particularly shown and described with references to preferred embodiments thereof, it will be understood by those skilled in the art that various changes in form and details may be made therein without departing from the scope of the invention encompassed by the appended claims.

What is claimed is:
1. A method of performing a procedure on an intervertebral disc of a functional spine unit comprising:

advancing at least a portion of a distal end of an implantation instrument into disc tissue, wherein said implantation instrument comprises a probe;

wherein said probe is releasably coupled to an implant;

wherein the implant is coupled to an anchor;

wherein said anchor is configured to penetrate a portion of a vertebral body adjacent the intervertebral disc;

retracting at least a portion of the implantation instrument such that at least a portion of the implant is placed between an anulus lamella and a portion of a nucleus of the intervertebral disc; and implanting at least a portion of said anchor in the adjacent vertebral body.

2. The method of claim 1, further comprising implanting at least a portion of a second anchor within said anulus or said adjacent vertebral body and connecting the second anchor to the first anchor.

3. The method of claim 2, further comprising providing tension between said first and second anchors to close a defect in the anulus.

4. The method of claim 1, wherein the implant comprises a barrier.

5. The method of claim 4, further comprising connecting said barrier to said anchor.

6. The method of claim 1, further comprising removing the implantation instrument comprising the probe from the functional spine unit.

7. A method of performing a procedure on an intervertebral disc of a functional spine unit comprising:

identifying an anulus of an intervertebral disc, wherein the anulus comprises a defect;

advancing at least a portion of a distal end of a delivery device comprising a distal intradiscal component located at the distal end of said delivery device into a portion of the intervertebral disc;

wherein the distal intradiscal component is releasably coupled to an implant comprising an anchor;

wherein said anchor is configured to penetrate a portion of a vertebral body adjacent to the intervertebral disc;

positioning at least a portion of said implant between the anulus and a portion of a nucleus of the intervertebral disc; and positioning at least a portion of said anchor the adjacent vertebral body.

8. The method of claim 7, further comprising implanting at least a portion of a second anchor within said anulus or said adjacent vertebral body in addition to said anchor and connecting the second anchor to said anchor.

9. The method of claim 8, further comprising providing tension between said anchors to close said defect.

10. The method of claim 7, wherein the implant comprises a barrier.

11. The method of claim 10, further comprising connecting said barrier to said anchor.

12. The method of claim 7, further comprising removing the delivery device comprising the distal intradiscal component from the functional spine unit.

13. A method of performing a procedure on an intervertebral disc of a functional spine unit comprising:

identifying a defect in an anulus of an intervertebral disc;

advancing at least a portion of a distal end of a delivery device comprising a distal intradiscal component located at a distal end of said delivery device into a portion of the intervertebral disc;

wherein the distal intradiscal component is releasably coupled to an implant comprising an anchor;

wherein said anchor is configured to penetrate a portion of a vertebral body adjacent the intervertebral disc;

positioning at least a portion of said implant between the anulus and a portion of a nucleus of the intervertebral disc; and inserting at least a portion of said anchor in the adjacent vertebral body.

14. The method of claim 13, further comprising implanting at least a portion of a second anchor within said anulus or said adjacent vertebral body in addition to said anchor and connecting the second anchor to said anchor.

15. The method of claim 14, further comprising providing tension between said anchors to close said defect.

16. The method of claim 13, wherein the implant comprises a barrier.

17. The method of claim 16, further comprising connecting said barrier to said anchor.

18. The method of claim 13, further comprising removing the delivery device comprising the distal intradiscal component from the functional spine unit.

* * * * *